US006187806B1

(12) United States Patent
Steiner et al.

(10) Patent No.: US 6,187,806 B1
(45) Date of Patent: Feb. 13, 2001

(54) N-LINKED SULFONE OF HETEROCYCLIC THIOESTER HAIR GROWTH COMPOSITIONS AND USES

(75) Inventors: Joseph P. Steiner, Finksburg; Gregory S. Hamilton, Catonsville, both of MD (US)

(73) Assignee: GPI NIL Holdings, Wilmington, DE (US)

( * ) Notice: Under 35 U.S.C. 154(b), the term of this patent shall be extended for 0 days.

(21) Appl. No.: 09/359,709

(22) Filed: Jul. 23, 1999

Related U.S. Application Data

(60) Division of application No. 09/089,375, filed on Jun. 3, 1998, now Pat. No. 6,004,993, which is a continuation-in-part of application No. 08/869,426, filed on Jun. 4, 1997, now Pat. No. 5,945,441.

(51) Int. Cl.[7] .................................................. A06K 31/40
(52) U.S. Cl. ......................... 514/428; 514/277; 514/336; 514/342; 514/343; 514/880
(58) Field of Search ................................... 514/428, 277, 514/336, 342, 343, 880

(56) References Cited

U.S. PATENT DOCUMENTS

| | | |
|---|---|---|
| 4,070,361 | 1/1978 | Petrillo, Jr. . |
| 4,310,461 | 1/1982 | Krapcho et al. . |
| 4,374,829 | 2/1983 | Harris et al. . |
| 4,390,695 | 6/1983 | Krapcho et al. . |
| 4,438,031 | 3/1984 | Winkley et al. . |
| 4,531,964 | 7/1985 | Shimano et al. . |
| 4,574,079 | 3/1986 | Gavras et al. . |
| 4,578,474 | 3/1986 | Krapcho et al. . |
| 4,593,102 | 6/1986 | Shanklin, Jr. . |
| 4,808,573 | 2/1989 | Gold et al. . |
| 4,818,749 | 4/1989 | Gold et al. . |
| 4,996,193 | 2/1991 | Hewitt et al. . |
| 5,147,877 | 9/1992 | Goulet . |
| 5,189,042 | 2/1993 | Goulet et al. . |
| 5,192,773 | 3/1993 | Armistead et al. . |
| 5,208,241 | 5/1993 | Ok et al. . |
| 5,252,579 | 10/1993 | Skotnicki et al. . |
| 5,258,389 | 11/1993 | Goulet et al. . |
| 5,284,826 | 2/1994 | Eberle . |
| 5,284,840 | 2/1994 | Rupprecht et al. . |
| 5,284,877 | 2/1994 | Organ et al. . |
| 5,292,747 | 3/1994 | Davis et al. . |
| 5,294,603 | 3/1994 | Rinehart . |
| 5,319,098 | 6/1994 | Burbaum et al. . |
| 5,330,993 | 7/1994 | Armistead et al. . |
| 5,342,625 | 8/1994 | Hauer et al. . |
| 5,359,138 | 10/1994 | Takeuchi et al. . |
| 5,385,918 | 1/1995 | Connell et al. . |
| 5,414,083 | 5/1995 | Hackl et al. . |
| 5,424,454 | 6/1995 | Burbaum et al. . |
| 5,447,915 | 9/1995 | Schreiber et al. . |
| 5,457,111 | 10/1995 | Luly et al. . |
| 5,470,878 | 11/1995 | Michnick et al. . |
| 5,506,228 | 4/1996 | Norton et al. . |
| 5,516,797 | 5/1996 | Armistead et al. . |
| 5,532,248 | 7/1996 | Goulet et al. . |
| 5,543,423 | 8/1996 | Zelle et al. . |
| 5,614,547 | 3/1997 | Hamilton et al. . |
| 5,631,017 | 5/1997 | Sharpe et al. . |
| 5,703,088 | 12/1997 | Sharpe et al. . |
| 5,874,449 | * 2/1999 | Hamilton et al. ............... 514/330 |
| 5,945,441 | 8/1999 | Steiner et al. . |

FOREIGN PATENT DOCUMENTS

| | | |
|---|---|---|
| 3508251 | 9/1986 | (DE) . |
| 3931051 | 3/1990 | (DE) . |
| 4015255 | 11/1991 | (DE) . |
| 12401 | 6/1980 | (EP) . |
| 48159 | 3/1982 | (EP) . |
| 50800 | 5/1982 | (EP) . |
| 73143 | 3/1983 | (EP) . |
| 88350 | 9/1983 | (EP) . |
| 196841 | 10/1986 | (EP) . |
| 260118 | 3/1988 | (EP) . |
| 333174 | 9/1989 | (EP) . |
| 352000 | 1/1990 | (EP) . |
| 378318 | 7/1990 | (EP) . |
| 405994 | 1/1991 | (EP) . |
| 419049 | 3/1991 | (EP) . |
| 423714 | 4/1991 | (EP) . |
| 468339 | 1/1992 | (EP) . |
| 564924 | 10/1993 | (EP) . |
| 572365 | 12/1993 | (EP) . |
| 652229 | 5/1995 | (EP) . |
| 2247456 | 3/1992 | (GB) . |
| 04149166 | 5/1992 | (JP) . |
| 05178824 | 7/1993 | (JP) . |
| WO 88 00040 | 1/1988 | (WO) . |
| WO8809789 | 12/1988 | (WO) . |
| WO9012805 | 11/1990 | (WO) . |
| WO9104985 | 4/1991 | (WO) . |
| WO9113088 | 9/1991 | (WO) . |
| WO9200278 | 1/1992 | (WO) . |
| WO9204370 | 3/1992 | (WO) . |
| WO9216501 | 10/1992 | (WO) . |
| WO9218478 | 10/1992 | (WO) . |
| WO9219593 | 11/1992 | (WO) . |
| WO9219745 | 11/1992 | (WO) . |
| WO9221313 | 12/1992 | (WO) . |
| WO9307269 | 4/1993 | (WO) . |
| WO9313066 | 7/1993 | (WO) . |

(List continued on next page.)

OTHER PUBLICATIONS

Birkenshaw, T.N. et al., "Synthetic FKBP12 Ligands. Design and Synthesis of Pyranose Replacements," *Bioorganic & Medicinal Chemistry Letters*, (1994) 4:21, 2501–2506.

(List continued on next page.)

*Primary Examiner*—Rebecca Cook
(74) *Attorney, Agent, or Firm*—Nath & Associates PLLC; Gary M. Nath; Lee C. Heiman

(57) ABSTRACT

This invention relates to pharmaceutical compositions and methods for treating alopecia and promoting hair growth using N-linked sulfonamides of heterocyclic thioesters.

15 Claims, 5 Drawing Sheets

FOREIGN PATENT DOCUMENTS

| | | |
|---|---|---|
| WO9323548 | 11/1993 | (WO) . |
| WO9325546 | 12/1993 | (WO) . |
| WO9405639 | 3/1994 | (WO) . |
| WO9407858 | 4/1994 | (WO) . |
| WO9413629 | 6/1994 | (WO) . |
| WO9512572 | 5/1995 | (WO) . |
| WO9524385 | 9/1995 | (WO) . |
| WO9526337 | 10/1995 | (WO) . |
| WO9603318 | 10/1996 | (WO) . |
| WO9633184 | 10/1996 | (WO) . |
| WO9633187 | 10/1996 | (WO) . |
| WO9636630 | 11/1996 | (WO) . |
| WO 9641609 | 12/1996 | (WO) . |
| WO 9736869 | 10/1997 | (WO) . |
| WO9820891 | 5/1998 | (WO) . |
| WO9820892 | 5/1998 | (WO) . |
| WO9820893 | 5/1998 | (WO) . |
| WO9824805 | 6/1998 | (WO) . |
| 9207782 | 4/1993 | (ZA) . |

OTHER PUBLICATIONS

Caffrey, M.V. et al., "Synthesis and Evaluation of Dual Domain Macrocyclic FKBP12 Ligands," *Bioorganic & Medicinal Chemistry Letters*, (1994) 4:21, 2507–2510.

Hauske, J.R. et al. "Design and Synthesis of Novel FKBP Inhibitors," *J. of Medicinal Chemistry*, (1992) 35, 4284–4296.

Holt, D.A. et al., "Design, Synthesis, and Kinetic Evaluation of High–Affinity FKBP Ligands and the X–ray Crystal Structures of Their Complexes with FKBP12," *J. Am. Chem. Soc.*, (1993) 115, 9925–9938.

Holt, D.A. et al., "Structure–Activity Studies of Synthetic FKBP Ligands as Peptidyl–prolyl Isomers Inhibitors," *Bioorganic & Medicinal Chemistry Letters*, (1994) 4:2, 315–320.

Holt, D.A. et al., "Structure–Activity Studies of Nonmacrocyclic Rapamycin Derivatives," *Bioorganic & Medicinal Chemistry Letter*, (1993) 3:10, 1977–1980.

Iwabuchi, T. et al., "Effects of immunosuppressive peptidyl–prolyl cis–trans isomerase (PPIase inhibitors, cyclosporin A, FK506, ascomycin and rapamycin, on hair growth initiation in mouse: immunosuppression is not required for hair growth," *J. of Deramatol. Sci.*, (1995) 9:1, 64–69.

Jiang, H. et al., "Induction of anagen in telogen mouse skin by topical application of FK506, a potent immunosuppressant," *J. Invest. Dermatol.*, (1995) 104:4, 523–525.

Luengo, J.I. et al., "Synthesis and Structure–Activity Relationships of Macrocyclic FKBP Ligands," *Bioorganic & Medicinal Chemistry Letters*, (1994) 4:2, 321–324.

Snyder, S.H. et al., "Immunophilins and the Nervous System," *Nature Medicine*, (1995) 1:1, 32–37.

Teague, S.J. et al., "Synthesis and Study of a Non–Macrocyclic FK506 Derivative," *Bioorganic & Medicinal Chemistry Letters*, (1994) 4:13, 1581–1584.

Teague, S.J. et al., "The Affinity of the Excised Binding Domain of FK–506 for the Immunophilin FKBP12," *Bioorganic & Medicinal Chemistry Letters*, (1993) 3:10, 1947–1950.

Wang, G.T. et al., "Synthesis and FKBP Binding of Small Molecule Mimics of the Tricarbonyl Region of FK506," *Bioorganic and Medicinal Chemistry Letters*, (1994) 4:9, 1161–1166.

Yamashita, D.S. et al., "Design, Synthesis and Evaluation of Dual Domain FKBP Ligands," *Bioorganic & Medicinal Chemistry*, (1994) 4:2, 325–328.

Yamamoto, S. et al., "Stimulation of hair growth by topical application of FK506, a potent immunosuppressive agent," *J. Invest. Dermatol*, (1994) 102:2, 160–164.

Ando, Takao et al., "Formation of Crossed Phenzine from the Reaction between Tetra–p–anisyl– and Tetra–p–tolyl–hydrazines in Liquid Sulphur Dioxide," Chem. Comm., S. Chem. Comm., 1975, 989.

Andrus, Merrit B., "Structure–based design of an acyclic ligand that bridges FKBP12 and calcineurin," J. Am. Chem. Soc., 1993, 115(2), 10420–1.

Armistead, D.M. et al., "Design, synthesis and structure of non–macrocyclic inhibitors of FKBP12, the major binding protin for the immunosuppressant FK506," Acta Crystallogr. 1995, D51(4), 522–8.

Askin, D. et al., "Chemistry of FK–506: benzilic acid rearrangement of the tricarbonyl system," Tetrahedron Lett., 1989, 30(6), 671–4.

Askin, D. et al., "Effecient Degradation of FK–506 to a versatile synthetic intermediate," J. Org. Chem., 1990, 55(20), 5451–4.

Baader, Ekkehard et al., "Inhibition of prolyl 4–hydroxylase by oxalyl amino acid derivatives in vitro, in isolated microsomes and in embryonic chicken tissues," Biochem. J., 1994, 300(2), 525–30.

Baumann, K. et al., "Synthesis and oxidative cleavage of the major equilibrium products of ascomycin and Fk 506," Tetrahedron Lett., 1995, 26(13), 2231–4.

Bender, D., et al., "Periodate oxidation of α–keto γ–lactams. Enol oxidation and β–lactam formation. Mechanism of periodate hydroxylation reactions," J. Org. Chem., 1978, 43(17), 3354–62.

Boulmedais, Ali et al., "Stereochemistry of Electrochemical Reduction of Optically Active α–ketoamides. II. Electroreduction of benzoylformamides derived from S–(–)–proline," Bull. Soc. Chim. Fr., 1989, (2), 185–91. (French).

Cameron, Andrew et al., "Immunophilin FK506 binding protein associated with inositol 1,4,5–triphosphate receptor modulates calcium flux," Proc. Natl. Acad. Sci. USA, 1995, 92, 1784–1788.

Caufield, Craig E. and Musser, John H., "Macrocyclic Immunomodulators," Annual Reports in Medicinal Chemistry, Johns (Ed.), Academic Press, Chapter 21, 195–204, 1989.

Chakraborty, TK et al., "Design and Synthesis of a rapamycin–based high affinity binding FKBP12 ligand," Chem. Biol., 1995, 2(3), 157–61.

Chakaraborty, Tushar K., "Studies towards the development of cyclic peptide–based analogs of macrolide immunosuppressants," Pure Appl. Chem., 1996, 68(3), 565–568.

Coleman, R., and Danishefsky, S., "Degradation and manipulations of the immunosuppressant FK506: preparation of potential synthetic intermediates," Heterocycles, 1989, 28(1), 157–61.

Colombo, L. et al., "Enantioselective synthesis of secondary alcohols in the presence of chiral ligands," Tetrahedron, 1982, 38(17), 2725–7.

Cunliffe, C. Jane et al., "Novel inhibitors of prolyl 4–hydroxylase. 3. Inhibition by the substrate analog N–oxaloglycine and its derivatives," J. Med. Chem., 1992, 35 (14), 2652–8.

Cushman, D.W. et al., "Design of potent competitive inhibitors of angiotensin–converting enzyme. Carboxyalkanoyl and mercaptoalkanoyl amino acids," Biochemistry, 1977, 16(25), 5484–91.

Dawson, Ted M. et al., "Immunosuppressant FK506 enhances phosphorylation of nitric oxide synthase and protects against glutamate neurotoxicity," Proc. Natl. Acad. Sci. USA, 1993, 90, 9808–12.

Dawson, T.M. et al., "The immunophilins, FK506 binding and cyclophilin, are discretely localized in the brain: relationship to calcineurin," Neuroscience, 1994, 62(2), 569–80.

Effenberger F. et al., "Diastereoselective addition of benzenesulfenyl chloride to 1–acryloylproline esters," Chemical Abstracts, 1989, 110:154846h.

Egbertson, M. and Danishefsky, S., "A synthetic route to the tricarbonyl region of FK–506," J. Org. Chem., 1989, 54(1), 11–12.

Feutren, Gilles, "The Optimal use of Cyclosporin A in Autoimmune Diseases," J. of Autoimmunity, 1992, 5, 183–95.

Finberg, Robert W. et al., "Prevention of HIV–1 Infection and Preservation of CD4 Function by the Binding of CPFs to gp120," Science, 1990, 249, 287–91.

Fisher, Matthew et al., "On the remarkable propensity for carbon—carbon bond cleavage reactions in teh C(8)–C(10) region of FK–506," J. Org. Chem., 1991, 56(8), 2900–7.

Fry, Lionel, "Psoriasis: Immunopathology and Long–term treatment with Cyclosporin," J. of Autoimmunity, 1992, 5, 277–83.

Furber, Mark, "FKBP–12–ligand–calceineurin interactions: analogs of SBL506," J. Am. Chem. Soc., 1995, 117(27), 7267–8.

Furber, M. et al., "Studies relating to the immunosuppressive activity of FK506," Tetrahedron Lett., 1993, 34(8), 1351–4.

Goodfellow, Val S. et al., "p–Nitrophenyl 3–diazopyruvate and diazopyruvamides, a New Family of Photoactivatable Cross–Linking Bioprobes," Biochemistry, 28(15), 6346–60.

Goulet, Mark T., and Boger, Joshua, "Degradative studies on the tricarbonyl containing macrolide rapamycin," Tetrahedron Lett., 1990, 31(34), 4845–8.

Goulet, Mark T. and Boger, Joshua, "Degradative studies on the tricarbonyl containing macrolide rapamycin," Tetrahedron Lett., 1992, 32(45), 6454.

Haeusler, Johannes and Schmidt, Ulrich, "Amino acids and peptides. IX. Pyruv oyl amino acids," Chem. Ber., 1974, 107(1), 145–51. (German).

Harding, M.W., et al., "A receptor for the immunosuppressant FK506 is a cis–trans peptidyl–prolyl isomerase," Nature Lett., 1989, 341, 758–60.

Hauske, James R. et al., "Investigation of the effects of synthetic, non–cytotoxic immunophilin inhibitors on MDR," Bioorg. Med. Chem.. Lett., 1994, 4(17), 2097–102.

Hayward, C.M. et al., "Total Synthesis of rapamycin via a novel titanium–mediated aldol macrocyclization reaction," J. Am. Chem. Soc., 1993, 115(20), 9345–6.

Hayward, C.M. et al., "An application of the Suarez reaction to the regiospecific synthesis of the $C_{28}$–$C_{42}$ segment of rapamycin," 3989–92.

Hearn, Walter R., and Worthington, Robert E., "L–Proline–N–oxalic anhydride," J. Org. Chem., 1967, 32(12), 4072–4.

Jones, T. et al., "Chemistry of tricarbonyl hemiketals and application of Evans technology to the total synthesis of the immunosuppressant (–)–FK–506," J. Am. Chem. Soc., 1990, 112(8), 2998–3017.

Jones, A. et al., "A formal synthesis of FK–506. Exploration of some alternatives to macrolactamization," J. Org. Chem., 1990, 55(9), 2786–97.

Kaczmar, et al., Makromol. Chem., 1976, 177, 1981–9 (German).

Karle, Isabella L. et al., "Coformation of the oxalamide group in retro–bispeptides. Three crystal structures," Int. J. Pept. Protein Res., 1994, 43(2), 160–5.

Kino, Toru et al., "FK–506, A novel immunosuppressnt isolateded from A streptomyces," J. of Antibiotics, 1987, 40(9), 1249–55.

Kocienski, P. et al., "A synthesis of the C(1)–C(15) segment of tsukubaenolide (FK506)," Tetrahedron Lett., 1988, 29(35), 4481–4.

Krit, N.A. et al., "Impact of the nature of alkyl radical on the biological activity of N–carboxyalkyl dipeptides," Khim.–Farm. Zh., 1991, 25(7), 44–6. (Russian).

Linde, Robert G. et al., "Straightforward synthesis of 1,2, 3–tricarbonyl systems," J. Org. Chem., 1991, 56(7), 2534–8.

Luengo, J. et al., "Structure–activity studies of rapamycin analogs: evidence that the C–7 methodoxy group is part of the effector domain and positioned at the FKBP:12–FRAP interface," Chem. Biol., 1995, 2(7), 471–81.

Luengo, Juan I. et al., "Efficient removal of pipecolinate from rapamycin and FK506 by reaction with tetrabutylammonium cyanide," Tetrahedron Lett., 1993, 34(29), 4599–602.

Luengo, J. et al., "Studies on the chemistry of rapamycin: novel transformation under Lewis–acid catalysis," Tetrahedron Lett., 1993, 34(6), 991–4.

Lyons, W. Ernest et al., "Neronal Regeneration Enhances the Expression of the Immunophilin FKBP–12," The Journal of Neuroscience, 1995, 15, 2985–94.

Marshall, J.A. et al., Convenient synthesis of dioxopiperazines via aminolysis of .alpha.–(pyruvylamino) esters, Synth. Commun., 1975, 5(3), 237–44.

Mashkovskii, M.D. et al., "1–[4–(2–Hydroxy–3–tert–butylaminopropoxy)–indole–3–yl (5–acetamido–1–(S)–carboxypentyl)–DL–alanyl]–L–proline dihydrochloride, a new angiotensin–converting enzyme inhibitor with β–adrenoblocking properties," Khim.–Farm. Zh., 1993, 27(10), 16–20. (Russian).

Munegumi, Toratane et al., "Asymmetric Catalytic Hydrogenations of N–pyruvoyl–(S)–proline esters," Bull. Chem. Soc. Jpn., 1987, 60(1), 243–53.

Munoz, Benito et al., "α–Ketoamide Phe–Pro isostere as a new core structure for the inhibition of HIV protease," Bioorg. Med. Chem., 1994, 2(10), 1085–90.

Nakatsuka, M et al. " Total Synthesis of FK506 and an FKBP Reagent, $(C_8, C_9–^{13}C_2)$–FK–506," J. Am. Chem. Soc., 1990, 112 (14), 5583–90.

Nelson, F. et al., "A novel ring contraction of rapamycin," Tetrahedron Lett., 1994, 35(41), 7557–60.

Pattenden, Gerald and Tankard, Mark, "Facile Synthesis of the tricarbonyl subunit in the immunosuppressant rapamycin," Tetrahedron Lett., 1993, 34(16), 2677–80.

Ponticelli, Claudio, "Treatment of the Nephrotic Syndrome with Cyclosporin A," J. of Autoimmunity, 1992, 5, 315–24.

Ranganathan, Darshan et al., "Protein Backbone Modification by Novel Cα–C Side–Chain Scission," 1994, J. Am. Chem. Soc., 116(15), 6545–57.

Rao, A.V., et al., "Studies directed towards the synthesis of immunosuppressive agent FK–506: construction of the tricarbonyl moiety," Tetrahedron Lett., 1990, 31(10), 1439–42.

Rao, A.V. Rama et al., "Studies directed towards the synthesis of immunosuppressive agent FK–506: synthesis of the entire bottom half," Tetrahedron Lett., 1991, 32(9), 1251–4.

Rao, A.V. Rama and Desibhatla, Vidyanand, "Studies directed towards the syntesis of rapamycin: stereoselective synthesis of C–1 to C–15 segment," Tetrahedron Lett., 1993, 34(44), 7111–14.

Skotnicki, Jerauld et al., "Ring expanded rapamycin derivatives," Tetrahedron Lett., 1994, 35(2), 201–2.

Skotnicki, Jerauld et al., "Synthesis of secorapamycin esters and amides," Tetrah. Lett., 1994, 35(2), 197–200.

Slee, Deborah H. et al., Selectivity in the Inhibition of HIV and FIV Protease: Inhibitory and Mechanistic Studies of Pyrrolidine–Containing α–Keto Amide and Hydroxyethylamine Core Structures, J. Am. Chem. Soc., 1995, 117(48), 1187–78.

Soai, Kenso et al., "Asymmetric Allylation of α–keto amides Derived from (S)–proline esters," Pept. Chem., 1986, 24, 327–330.

Soai, Kenso and Ishizaki, Miyuki, "Asymmetric Synthesis of Functionalized tertiary alcohols by diastereoselective allylation of chiral α–keto amides derived from (S)–proline esters: control of stereochemistry based on saturated coordination of Lewis acid," J. Org. Chem., 1986, 57(17) 3290–5. (English).

Soai, Kenso et al., "Asymmetric synthesis of both eaniomers of α–hydroxy acids by the diastereoselective reduction of chiral α–keto amides with complex metal hydrides in the presence of a metal salt," Chem. Lett., 1986, 11, 1897–900.

Soai, Kenso and Hasegawa, Hitoshi, "Diastereoselective reduction of chiral α–ketoamides derived from (S)–proline esters with sodium borohydride. Preparation of optically active α–hydroxy acids," J. Chem. Soc., 1985, 1(4), 769–72.

Soai, Kenso and Ishizaki, Miyuki, "Diastereoselective asymmetric allylation of chiral α–keto amides with allyltrimethylsilane. Preparation of protected homoallylic alcohols," J. Chem. Soc., 1984, 15, 1016–1017.

Steffan, Robert J. et al., "Base catalyzed degradations of rapamycin," Tetrahedron Lett., 1993, 34(23), 3699–702.

Steglich, Wolfgang and Hinze, Sabine, "A rational synthesis of N–trifluroacetylamino acids," Synthesis, 1976, 8, 399–401. (German).

Steglich, Wolfgang et al., "Activated carboxylic acid derivatives. II. A simple synthesis of 2–oxycarboxylic acid amides, N–(2–oxoacyl) amino acid esters and 2–oxocarboxylic acid hydrazides," Synthesis, 1978, 8, 622–4. (German).

Steiner, Joseph P. et al., "High brain densities of the immunophilin FKBP colocalized with calcineurin," Nature Lett., 1992, 358, 584–7.

Steiner, J.P. et al., "Nonimmunosuppressive Ligands for Neuroimmunophilins Promote Nerve Extension In Vitro and In Vivo," Society for Neuroscience Abstracts, 1996, 22, 297.13.

Stocks, M. et al., "The contribution to the binding of the pyranoside sustituents in the excised binding domain of FK–506," Bioorg. Med. Chem. Lett., 1994, 4(12), 1457–60.

Stocks, M. et al., "Macrocyclic ring closures employing the intramolecular Heck reaction," Tetrahedron Lett., 1995, 36(36), 6555–8.

Tanaka, H. et al., "Structure of FK506, a novel imunosuppressant isolated from Streptomyces," J. Am. Chem. Soc., 1987, 109(16), 5031–3.

Tatlock, J. et al., "High affinity FKBP–12 ligands from (R)–(–)–carvone. Synthesis and evaluation of FK506 pyranose ring replacements," Bioorg. Med. Chem. Lett., 1995, 5(21), 2489–94.

Teague, S. et al., "Synthesis of FK506–cyclosporin hybrid macrocycles," Bioorg. Med. Chem. Lett., 1995, 5(20), 2341–6.

Tugwell, Peter, "Clyclosporin in the Treatment of Rheumatoid Arthritis," J. of Autoimmunity, 1992, 5, 231–40.

Wang, C.P. et al., "High performance liquid chromatographic isolation and spectroscopic characterization of three major metabolites from the plasma of rats receiving rapamycin (sirolimus) orally," J. Liq. Chromatogr., 1995, 18(13), 2559–68.

Wang, C.P. et al., "A high performance liquid chromatographic method for the determination of rapamycin {sirolimus} in rat serum, plasma, and blood and in monkey serum," J. Liq. Chromatogr., 1995, 18(9), 1801–8.

Whitesell, J.K. et al., "Asymmetric Induction. Reduction, Nucleophilic Addition to, Ene Reactions of Chiral α–Ketoesters," J. Chem. Soc., Chem Commun., 1983, 802.

Williams, D.R. and Benbow, J.W., "Synthesis of the α,β diketo amide segment of the novel immunosuppressive FK506," J. Org. Chem., 1988, 53(191), 4643–4.

Yohannes, Daniel et al., "Degradation of rapamycin: synthesis of a rapamycin–derived fragment containing the tricarbonyl and triene sectors,"Tetrahedron Lett., 1993, 34(13), 2075–8.

* cited by examiner

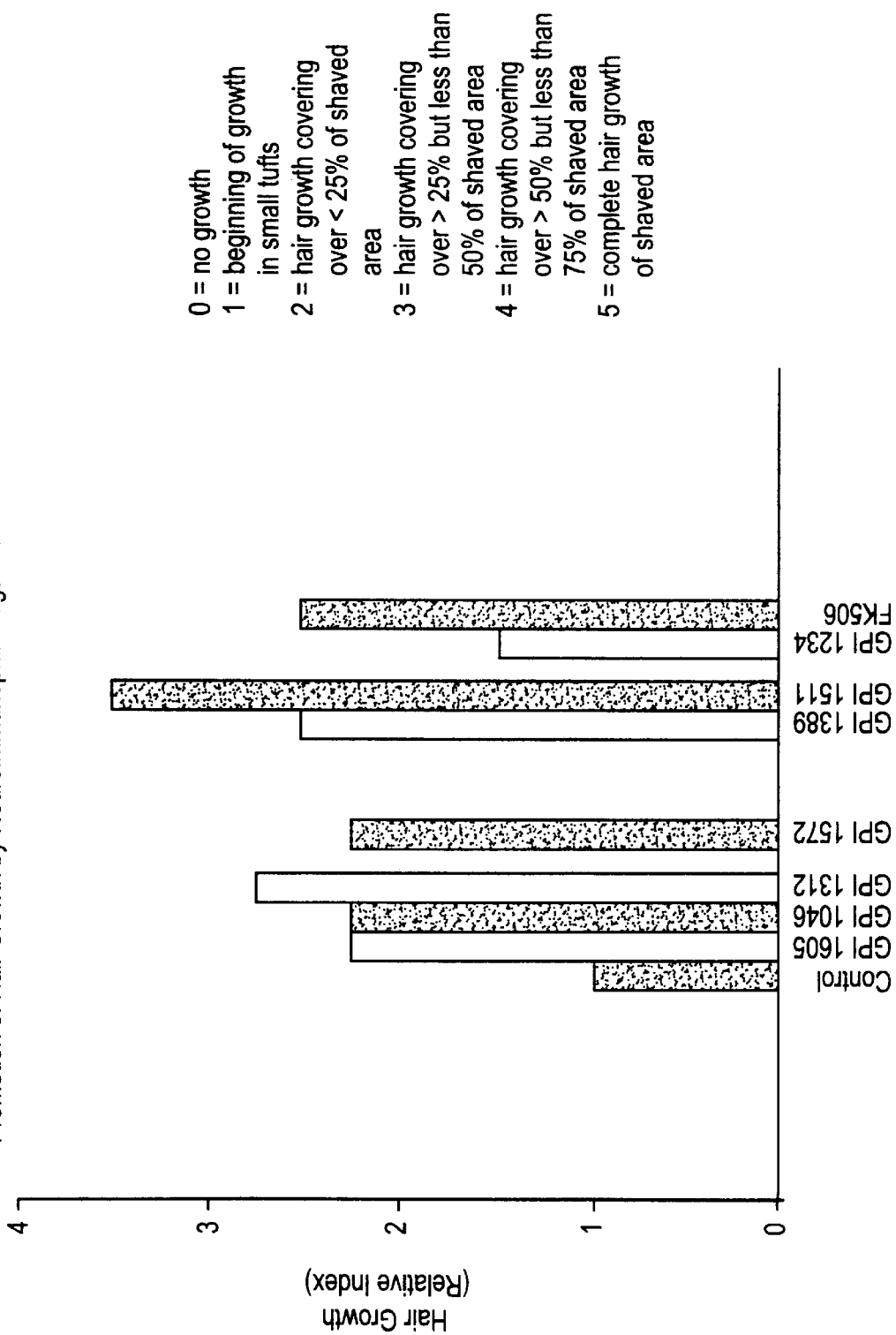

US 6,187,806 B1

N-LINKED SULFONE OF HETEROCYCLIC THIOESTER HAIR GROWTH COMPOSITIONS AND USES

This application is a divisional application of U.S. patent application Ser. No. 09/089,375, filed on Jun. 3, 1998, now U.S. Pat. No. 6,004,993 which is in turn a continuation-in-part of U.S. patent application Ser. No. 08/869,426, filed on Jun. 4, 1997, now U.S. Pat. No. 5,945,441 the entire contents of which are incorporated by reference herein as though set forth in full.

BACKGROUND OF THE INVENTION

1. Field of Invention

This invention relates to pharmaceutical compositions and methods for treating alopecia and promoting hair growth using low molecular weight, small molecule N-linked sulfones of heterocyclic thioesters.

2. Description of Related Art

Hair loss occurs in a variety of situations. These situations include male pattern alopecia, alopecia senilis, alopecia areata, diseases accompanied by basic skin lesions or tumors, and systematic disorders such as nutritional disorders and internal secretion disorders. The mechanisms causing hair loss are very complicated, but in some instances can be attributed to aging, genetic disposition, the activation of male hormones, the loss of blood supply to hair follicles, and scalp abnormalities.

The immunosuppressant drugs FK506, rapamycin and cyclosporin are well known as potent T-cell specific immunosuppressants, and are effective against graft rejection after organ transplantation. It has been reported that topical, but not oral, application of FK506 (Yamamoto et al., J. Invest. Dermatol., 1994, 102, 160–164; Jiang et al., J. Invest. Dermatol. 1995, 104, 523–525) and cyclosporin (Iwabuchi et al., J. Dermatol. Sci. 1995, 9, 64–69) stimulates hair growth in a dose-dependent manner. One form of hair loss, alopecia areata, is known to be associated with autoimmune activities; hence, topically administered immuno-modulatory compounds are expected to demonstrate efficacy for treating that type of hair loss. The hair growth stimulating effects of FK506 have been the subject of an international patent filing covering FK506 and structures related thereto for hair growth stimulation (Honbo et al., EP 0 423 714 A2). Honbo et al. discloses the use of relatively large tricyclic compounds, known for their immunosuppressive effects, as hair revitalizing agents.

The hair growth and revitalization effects of FK506 and related agents are disclosed in many U.S. patents (Goulet et al., U.S. Pat. No. 5,258,389; Luly et al., U.S. Pat. No. 5,457,111; Goulet et al., U.S. Pat. No. 5,532,248; Goulet et al., U.S. Pat. No. 5,189,042; and Ok et al., U.S. Pat. No. 5,208,241; Rupprecht et al., U.S. Pat. No. 5,284,840; Organ et al., U.S. Pat. No. 5,284,877).

These patents claim FK506 related compounds. Although they do not claim methods of hair revitalization, they disclose the known use of FK506 for effecting hair growth. Similar to FK506 (and the claimed variations in the Honbo et al. patent), the compounds claimed in these patents are relatively large. Further, the cited patents relate to immuno-modulatory compounds for use in autoimmune related diseases, for which FK506's efficacy is well known.

Other U.S. patents disclose the use of cyclosporin and related compounds for hair revitalization (Hauer et al., U.S. Pat. No. 5,342,625; Eberle, U.S. Pat. No. 5,284,826; Hewitt et al., U.S. Pat. No. 4,996,193). These patents also relate to compounds useful for treating autoimmune diseases and cite the known use of cyclosporin and related immunosuppressive compounds for hair growth.

However, immunosuppressive compounds by definition suppress the immune system and also exhibit other toxic side effects. Accordingly, there is a need for non-immunosuppressant, small molecule compounds which are useful as hair revitalizing compounds.

Hamilton and Steiner disclose in U.S. Pat. No. 5,614,547 novel pyrrolidine carboxylate compounds which bind to the immunophilin FKBP12 and stimulate nerve growth, but which lack immunosuppressive effects. Unexpectedly, it as been discovered that these non-immunosuppressant compounds promote hair growth with an efficacy similar to FK506. Yet their novel small molecule structure and non-immuno-suppressive properties differentiate them from FK506 and related immunosuppressive compounds found in the prior art.

SUMMARY OF THE INVENTION

The present invention relates to a method for treating alopecia or promoting hair growth in an animal, which comprises administering to said animal an effective amount of an N-linked sulfone of heterocyclic thioester.

The present invention further relates to a pharmaceutical composition which comprises:

(i) an effective amount of an N-linked sulfone of heterocyclic thioester for treating alopecia or promoting hair growth in an animal; and (ii) a pharmaceutically acceptable carrier.

The N-linked sulfone of heterocyclic thioester used in the inventive methods and pharmaceutical compositions have an affinity for FKBP-type immunophilins and do not exert any significant immunosuppressive activity.

BRIEF DESCRIPTION OF THE DRAWINGS

FIG. 2 shows that less than 3% of the shaved area is covered with new hair growth when the vehicle (control) is administered.

FIG. 3 shows the remarkable effects of non-immunosuppressive neuro-immunophillin FKBP ligands, wherein 90% of the shaved area is covered with new hair growth.

FIG. 4 shows the remarkable ability of non-immunosuppressive neuro-immunophillin FKBP ligands to achieve, essentially, complete hair regrowth in the shaved area.

FIG. 5 is a bar graph depicting the relative hair growth indices for C57 Black 6 mice treated with a vehicle, FK506, and various non-immunosuppressive neuro-immunophilin FKBP ligands, including GPI 1312, 14 days after treatment with each identified compound. FIG. 5 demonstrates the remarkable early hair growth promoted by a wide variety of non-immunosuppressive neuroimmunophilin FKBP ligands.

DETAILED DESCRIPTION OF THE INVENTION

Definitions

Figure 1:
FIG. 1 is a photograph of C57 Black 6 mice before being shaved for the hair regeneration experiment.

"Alopecia" refers to deficient hair growth and partial or complete loss of hair, including without limitation androgenic alopecia (male pattern baldness), toxic alopecia, alopecia senilis, alopecia areata, alopecia pelada and trichotillomania. Alopecia results when the pilar cycle is disturbed. The most frequent phenomenon is a shortening of the hair growth or anagen phase due to cessation of cell proliferation. This results in an early onset of the catagen phase, and consequently a large number of hairs in the telogen phase during which the follicles are detached from the dermal papillae, and the hairs fall out. Alopecia has a number of etiologies, including genetic factors, aging, local and systemic diseases, febrile conditions, mental stresses, hormonal problems, and secondary effects of drugs.

"GPI 1605" refers to a compound of formula

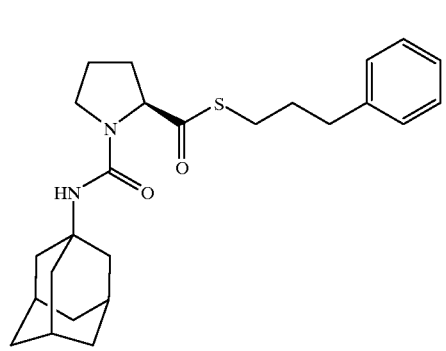

"GPI 1046" refers to 3-(3-pyridyl)-1-propyl(2s)-1-(3,3-dimethyl-1,2-dioxopentyl)-2-pyrrolidinecarboxylate, a compound of formula

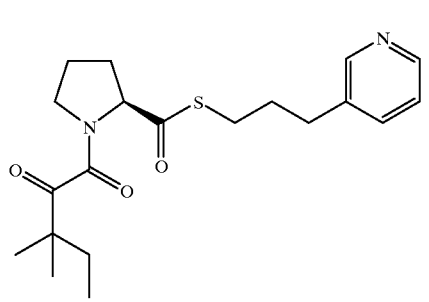

"GPI 1312" refers to a compound of formula

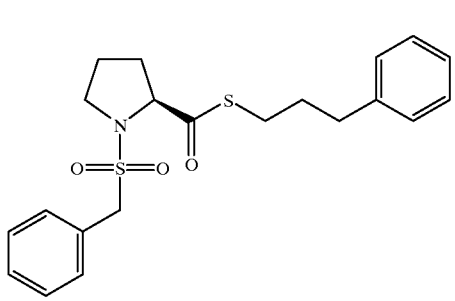

"GPI 1572" refers to a compound of formula

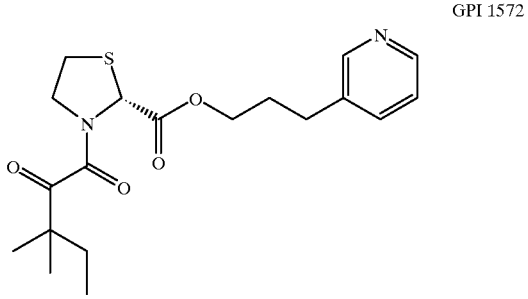

"GPI 1389" refers to a compound of formula

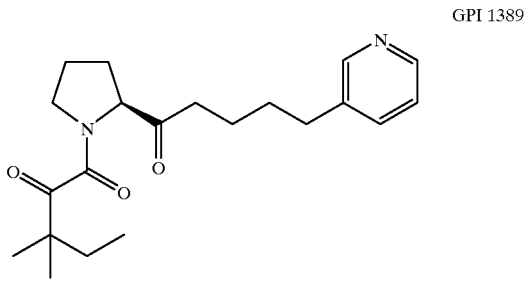

"GPI 1511" refers to a compound of formula

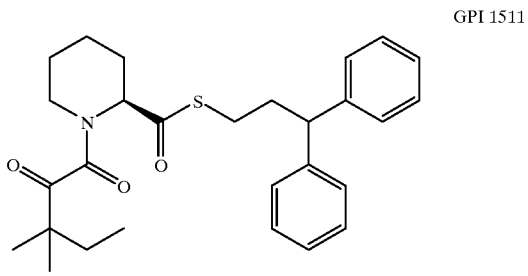

"GPI 12341" refers to a compound of formula

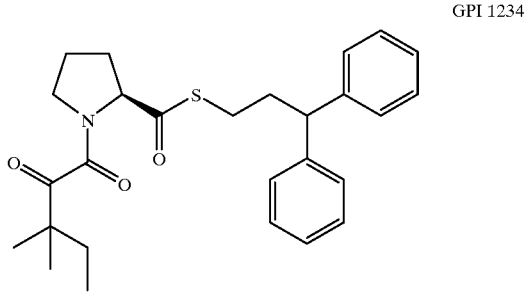

"Isomers" refer to different compounds that have the same molecular formula. "StereoisomersI" are isomers that differ only in the way the atoms are arranged in space. "Enantiomers" are a pair of stereoisomers that are non-superimposable mirror images of each other. "Diastereoisomers" are stereoisomers which are not mirror images of each other. "Racemic mixture" means a mixture containing equal parts of individual enantiomers. "Non-racemic mixture" is a mixture containing unequal parts of individual enantiomers or stereoisomers.

"Pharmaceutically acceptable salt, ester, or solvate" refers to a salt, ester, or solvate of a subject compound which possess the desired pharmacological activity and which is neither biologically nor otherwise undesirable. A salt, ester, or solvate can be formed with inorganic acids such as acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, gluconate, glycerophosphate, hemisulfate, heptanoate, hexanoate, hydrochloride, hydrobromide, hydroiodide, 2-hydroxyethanesulfonate, lactate, maleate, methanesulfonate, naphthylate, 2-naphthalenesulfonate, nicotinate, oxalate, sulfate, thiocyanate, tosylate and undecanoate. Examples of base salts, esters, or solvates include ammonium salts; alkali metal salts, such as sodium and potassium salts; alkaline earth metal salts, such as calcium and magnesium salts; salts with organic bases, such as dicyclohexylamine salts; N-methyl-D-glucamine; and salts with amino acids, such as arginine, lysine, and so forth. Also, the basic nitrogen-containing groups can be quaternized with such agents as lower alkyl halides, such as methyl, ethyl, propyl, and butyl chlorides, bromides, and iodides; dialkyl sulfates, such as dimethyl, diethyl, dibutyl, and diamyl sulfates; long chain halides, such as decyl, lauryl, myristyl, and stearyl chlorides, bromides, and iodides; aralkyl halides, such as benzyl and phenethyl bromides; and others. Water or oil-soluble or dispersible products are thereby obtained.

"Pilar cycle" refers to the life cycle of hair follicles, and includes three phases:

(1) the anagen phase, the period of active hair growth which, insofar as scalp hair is concerned, lasts about three to five years;

(2) the catagen phase, the period when growth stops and the follicle atrophies which, insofar as scalp hair is concerned, lasts about one to two weeks; and (3) the telogen phase, the rest period when hair progressively separates and finally falls out which, insofar as scalp hair is concerned, lasts about three to four months.

Normally 80 to 90 percent of the follicles are in the anagen phase, less than 1 percent being in the catagen phase, and the rest being in the telogen phase. In the telogen phase, hair is uniform in diameter with a slightly bulbous, non-pigmented root. By contrast, in the anagen phase, hair has a large colored bulb at its root.

"Promoting hair growth" refers to maintaining, inducing, stimulating, accelerating, or revitalizing the germination of hair.

"Treating alopecia" refers to:

(i) preventing alopecia in an animal which may be predisposed to alopecia; and/or (ii) inhibiting, retarding or reducing alopecia; and/or (iii) promoting hair growth; and/or (iv) prolonging the anagen phase of the hair cycle; and/or (v) converting vellus hair to growth as terminal hair. Terminal hair is coarse, pigmented, long hair in which the bulb of the hair follicle is seated deep in the dermis. Vellus hair, on the other hand, is fine, thin, non-pigmented short hair in which the hair bulb is located superficially in the dermis. As alopecia progresses, the hairs change from the terminal to the vellus type.

Methods of the Present Invention

The present invention relates to a method for treating alopecia or promoting hair growth in an animal, which comprises administering to said animal an effective amount of an N-linked sulfone of heterocyclic thioester.

The inventive method is particularly useful for treating male pattern alopecia, alopecia senilis, alopecia areata, alopecia resulting from skin lesions or tumors, alopecia resulting from cancer therapy such as chemotherapy and radiation, and alopecia resulting from systematic disorders such as nutritional disorders and internal secretion disorders.

Pharmaceutical Compositions of the Present Invention

The present invention also relates to a pharmaceutical composition comprising:

(i) an effective amount of an N-linked sulfone of heterocyclic thioester for treating alopecia or promoting hair growth in an animal; and (ii) a pharmaceutically acceptable carrier.

N-linked Sulfones of Heterocyclic Thioesters

The N-linked sulfones of heterocyclic thioesters used in the methods and pharmaceutical compositions of the present invention are low molecular weight, small molecule compounds having an affinity for FKBP-type immunophilins, such as FKBP12. When an N-linked sulfone of heterocyclic thioester binds to an FKBP-type immunophilin, it has been found to inhibit the prolyl-peptidyl cis-trans isomerase, or rotamase, activity of the binding protein. Unexpectedly, these compounds have also been found to stimulate hair growth. The compounds are devoid of any significant immunosuppressive activity.

Formula I

The N-linked sulfone of heterocyclic thioester may be a compound of formula I

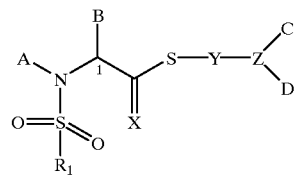

or a pharmaceutically acceptable salt, ester, or solvate thereof, wherein:

A and B, taken together with the nitrogen and carbon atoms to which they are respectively attached, form a 5–7 membered saturated or unsaturated heterocyclic ring containing, in addition to the nitrogen atom, one or more additional O, S, SO, $SO_2$, N, NH, or $NR_2$ heteroatom(s);

X is either O or S;

Y is a direct bond, $C_1$–$C_6$ straight or branched chain alkyl, or $C_2$–$C_6$ straight or branched chain alkenyl, wherein any carbon atom of said alkyl or alkenyl is optionally substituted in one or more position(s) with amino, halo, haloalkyl, thiocarbonyl, ester, thioester, alkoxy, alkenoxy, cyano, nitro, imino, alkylamino, aminoalkyl, sulfhydryl, thioalkyl, sulfonyl, or oxygen to form a carbonyl, or wherein any carbon atom of said alkyl or alkenyl is optionally replaced with O, NH, $NR_2$, S, SO, or $SO_2$ $R_2$ is selected from the group consisting of hydrogen, $C_1$–$C_4$ straight or branched chain alkyl, $C_3$–$C_4$ straight or branched chain alkenyl or alkynyl, and $C_1$–$C_4$ bridging alkyl wherein a bridge is formed between the nitrogen and a carbon atom of said alkyl or alkenyl chain containing said heteroatom to form a ring, wherein said ring is optionally fused to an Ar group;

Ar is an alicyclic or aromatic, mono-, bi- or tricyclic, carbo- or heterocyclic ring, wherein the ring is either unsubstituted or substituted with one or more substituent (s); wherein the individual ring size is 5–8 members; wherein the heterocyclic ring contains 1–6 heteroatom(s) independently selected from the group consisting of O, N, and S; wherein an aromatic or tertiary alkyl amine is optionally oxidized to a corresponding N-oxide;

Z is a direct bond, $C_1$–$C_6$ straight or branched chain alkyl, or $C_2$–$C_6$ straight or branched chain alkenyl, wherein any carbon atom of said alkyl or alkenyl is optionally substituted in one or more position(s) with amino, halo, haloalkyl, thiocarbonyl, ester, thioester, alkoxy, alkenoxy, cyano, nitro, imino, alkylamino, aminoalkyl, sulfhydryl, thioalkyl, sulfonyl, or oxygen to form a carbonyl, or wherein any atom of said alkyl or alkenyl is optionally replaced with O, NH, $NR_2$, S, SO, or $SO_2$;

C and D are independently hydrogen, Ar, $C_1$–$C_6$ straight or branched chain alkyl, or $C_2$–$C_6$ straight or branched chain alkenyl; wherein said alkyl or alkenyl is optionally substituted with one or more substituent(s) independently selected from the group consisting of $C_3$–$C_8$ cycloalkyl, $C_5$–$C_7$ cycloalkenyl, hydroxy, carbonyl oxygen, and Ar; wherein said alkyl, alkenyl, cycloalkyl or cycloalkenyl is optionally substituted with $C_1$–$C_6$ alkyl, $C_2$–$C_6$ alkenyl, hydroxy, amino, halo, haloalkyl, thiocarbonyl, ester, thioester, alkoxy, alkenoxy, cyano, nitro, imino, alkylamino, aminoalkyl, sulfhydryl, thioalkyl, or sulfonyl; wherein any carbon atom of said alkyl or alkenyl is optionally substituted in one or more position(s) with oxygen to form a carbonyl; or wherein any carbon atom of said alkyl or alkenyl is optionally replaced with O, NH, $NR_2$, S, SO, or $SO_2$; and $R_1$ is selected from the group consisting of Ar, $C_3$–$C_8$ cycloalkyl, $C_1$–$C_6$ straight or branched chain alkyl, and $C_2$–$C_6$ straight or branched chain alkenyl, wherein said alkyl or alkenyl is optionally substituted with one or more substituent(s) independently selected from the group consisting of Ar, $C_3$–$C_8$ cycloalkyl, amino, halo, haloalkyl, hydroxy, trifluoromethyl, $C_1$–$C_6$ straight or branched chain alkyl, $C_2$–$C_6$ straight or branched chain alkenyl, carbonyl, thiocarbonyl, ester, thioester, alkoxy, alkenoxy, cyano, nitro, imino, alkylamino, aminoalkyl, sulfhydryl, thioalkyl, and sulfonyl, wherein any carbon atom of said alkyl or alkenyl is optionally replaced with O, NH, $NR_2$, S, SO, or $SO_2$.

Useful carbo- and heterocyclic rings include without limitation phenyl, benzyl, naphthyl, indenyl, azulenyl, fluorenyl, anthracenyl, indolyl, isoindolyl, indolinyl, benzofuranyl, benzothiophenyl, indazolyl, benzimidazolyl, benzthiazolyl, tetrahydrofuranyl, tetrahydropyranyl, pyridyl, pyrrolyl, pyrrolidinyl, pyridinyl, pyrimidinyl, purinyl, quinolinyl, isoquinolinyl, tetrahydroquinolinyl, quinolizinyl, furyl, thiophenyl, imidazolyl, oxazolyl, benzoxazolyl, thiazolyl, isoxazolyl, isotriazolyl, oxadiazolyl, triazolyl, thiadiazolyl, pyridazinyl, pyrimidinyl, pyrazinyl, triazinyl, trithianyl, indolizinyl, pyrazolyl, pyrazolinyl, pyrazolidinyl, thienyl, tetrahydroisoquinolinyl, cinnolinyl, phthalazinyl, quinazolinyl, quinoxalinyl, naphthyridinyl, pteridinyl, carbazolyl, acridinyl, phenazinyl, phenothiazinyl, and phenoxazinyl.

In a preferred embodiment of formula I, Ar is selected from the group consisting of phenyl, benzyl, naphthyl, indolyl, pyridyl, pyrrolyl, pyrrolidinyl, pyridinyl, pyrimidinyl, purinyl, quinolinyl, isoquinolinyl, furyl, fluorenyl, thiophenyl, imidazolyl, oxazolyl, thiazolyl, pyrazolyl, and thienyl.

In another preferred embodiment of formula I, A and B are taken together, with the nitrogen and carbon atoms to which they are respectively attached, to form a 6 membered saturated or unsaturated heterocyclic ring; and $R_2$ is $C_4$–$C_7$ branched chain alkyl, $C_4$–$C_7$ cycloalkyl, phenyl, or 3,4,5-trimethoxyphenyl.

In another preferred embodiment of formula I, the N-linked sulfone of heterocyclic thioester is the compound GPI 1312, of the formula

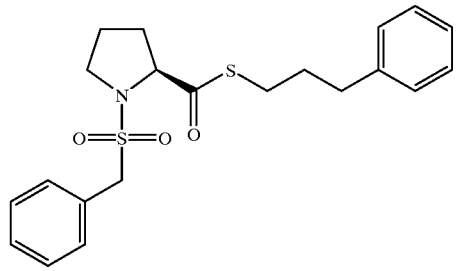

GPI 1312

In the most preferred embodiment of formula I, the compound is selected from the group consisting of:

3-(para-Methoxyphenyl)-1-propylmercaptyl(2S)-N-(benzenesulfonyl)pyrrolidine-2-carboxylate;

3-(para-Methoxyphenyl)-1-propylmercaptyl(2S)-N-(α-toluenesulfonyl)pyrrolidine-2-carboxylate;

3-(para-Methoxyphenyl)-1-propylmercaptyl(2S)-N-(α-toluenesulfonyl)pyrrolidine-2-carboxylate;

1,5-Diphenyl-3-pentylmercaptyl N-(para-toluenesulfonyl)pipecolate; and pharmaceutically acceptable salts, esters, and solvates thereof.

Formula II

The N-linked sulfone of heterocyclic thioester may also be a compound of formula II

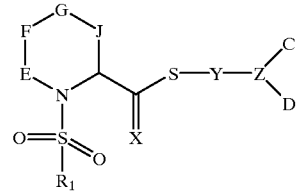

II or a pharmaceutically acceptable salt, ester, or solvate thereof, wherein:

E, F, G and J are independently $CH_2$, OS, SO, $SO_2$, NH or $NR_2$;

X is either O or S;

Y is a direct bond, $C_1$–$C_6$ straight or branched chain alkyl, or $C_2$–$C_6$ straight or branched chain alkenyl, wherein any carbon atom of said alkyl or alkenyl is optionally substituted in one or more position(s) with amino, halo, haloalkyl, thiocarbonyl, ester, thioester, alkoxy, alkenoxy, cyano, nitro, imino, alkylamino, aminoalkyl, sulfhydryl, thioalkyl, sulfonyl, or oxygen to form a carbonyl, or wherein any carbon atom of said alkyl or alkenyl is optionally replaced with O, NH, $NR_2$, S, SO, or $SO_2$;

R₂ is selected from the group consisting of hydrogen, $C_1$–$C_4$ straight or branched chain alkyl, $C_3$–$C_4$ straight or branched chain alkenyl or alkynyl, and $C_1$–$C_4$ bridging alkyl wherein a bridge is formed between the nitrogen and a carbon atom of said alkyl or alkenyl chain containing said heteroatom to form a ring, wherein said ring is optionally fused to an Ar group;

Z is a direct bond, $C_1$–$C_6$ straight or branched chain alkyl, or $C_2$–$C_6$ straight or branched chain alkenyl, wherein any carbon atom of said alkyl or alkenyl is optionally substituted in one or more position(s) with amino, halo, haloalkyl, thiocarbonyl, ester, thioester, alkoxy, alkenoxy, cyano, nitro, imino, alkylamino, aminoalkyl, sulfhydryl, thioalkyl, sulfonyl, or oxygen to form a carbonyl, or wherein any atom of said alkyl or alkenyl is optionally replaced with O, NH, NR₂, S, SO, or SO₂;

Ar is an alicyclic or aromatic, mono-, bi- or tricyclic, carbo- or heterocyclic ring, wherein the ring is either unsubstituted or substituted with one or more substituent(s); wherein the individual ring size is 5–8 members; wherein the heterocyclic ring contains 1–6 heteroatom(s) independently selected from the group consisting of O, N, and S; wherein an aromatic or tertiary alkyl amine is optionally oxidized to a corresponding N-oxide;

C and D are independently hydrogen, Ar, $C_1$–$C_6$ straight or branched chain alkyl, or $C_2$–$C_6$ straight or branched chain alkenyl; wherein said alkyl or alkenyl is optionally substituted with one or more substituent(s) independently selected from the group consisting of $C_3$–$C_8$ cycloalkyl, $C_5$–$C_7$ cycloalkenyl, hydroxy, carbonyl oxygen, and Ar; wherein said alkyl, alkenyl, cycloalkyl or cycloalkenyl is optionally substituted with $C_1$–$C_6$ alkyl, $C_2$–$C_6$ alkenyl, hydroxy, amino, halo, haloalkyl, thiocarbonyl, ester, thioester, alkoxy, alkenoxy, cyano, nitro, imino, alkylamino, aminoalkyl, sulfhydryl, thioalkyl, or sulfonyl; wherein any carbon atom of said alkyl or alkenyl is optionally substituted in one or more position(s) with oxygen to form a carbonyl; or wherein any carbon atom of said alkyl or alkenyl is optionally replaced with O, NH, NR, S, SO, or SO₂; and R₁ is selected from the group consisting of Ar, $C_3$–$C_8$ cycloalkyl, $C_1$–$C_6$ straight or branched chain alkyl, and $C_2$–$C_6$ straight or branched chain alkenyl, wherein said alkyl or alkenyl is optionally substituted with one or more substituent(s) independently selected from the group consisting of Ar, $C_3$–$C_8$ cycloalkyl, amino, halo, haloalkyl, hydroxy, trifluoromethyl, $C_1$–$C_6$ straight or branched chain alkyl, $C_2$–$C_6$ straight or branched chain alkenyl, carbonyl, thiocarbonyl, ester, thioester, alkoxy, alkenoxy, cyano, nitro, imino, alkylamino, aminoalkyl, sulfhydryl, thioalkyl, and sulfonyl, wherein any carbon atom of said alkyl or alkenyl is optionally replaced with O, NH, NR₂, S, SO, or SO₂.

Useful carbo- and heterocyclic rings include without limitation phenyl, benzyl, naphthyl, indenyl, azulenyl, fluorenyl, anthracenyl, indolyl, isoindolyl, indolinyl, benzofuranyl, benzothiophenyl, indazolyl, benzimidazolyl, benzthiazolyl, tetrahydrofuranyl, tetrahydropyranyl, pyridyl, pyrrolyl, pyrrolidinyl, pyridinyl, pyrimidinyl, purinyl, quinolinyl, isoquinolinyl, tetrahydroquinolinyl, quinolizinyl, furyl, thiophenyl, imidazolyl, oxazolyl, benzoxazolyl, thiazolyl, isoxazolyl, isotriazolyl, oxadiazolyl, triazolyl, thiadiazolyl, pyridazinyl, pyrimidinyl, pyrazinyl, triazinyl, trithianyl, indolizinyl, pyrazolyl, pyrazolinyl, pyrazolidinyl, thienyl, tetrahydroisoquinolinyl, cinnolinyl, phthalazinyl, quinazolinyl, quinoxalinyl, naphthyridinyl, pteridinyl, carbazolyl, acridinyl, phenazinyl, phenothiazinyl, and phenoxazinyl.

In a preferred embodiment of formula II, Ar is selected from the group consisting of phenyl, benzyl, naphthyl, indolyl, pyridyl, pyrrolyl, pyrrolidinyl, pyridinyl, pyrimidinyl, purinyl, quinolinyl, isoquinolinyl, furyl, fluorenyl, thiophenyl, imidazolyl, oxazolyl, thiazolyl, pyrazolyl, and thienyl.

Formula III

The N-linked sulfone of heterocyclic thioester may further be a compound of formula III

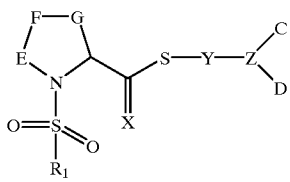

or a pharmaceutically acceptable salt, ester, or solvate thereof, wherein:

E, F, and G are independently CH₂, O, S, SO, SO₂, NH or NR₂;

X is either O or S;

Y is a direct bond, $C_1$–$C_6$ straight or branched chain alkyl, or $C_2$–$C_6$ straight or branched chain alkenyl, wherein any carbon atom of said alkyl or alkenyl is optionally substituted in one or more position(s) with amino, halo, haloalkyl, thiocarbonyl, ester, thioester, alkoxy, alkenoxy, cyano, nitro, imino, alkylamino, aminoalkyl, sulfhydryl, thioalkyl, sulfonyl, or oxygen to form a carbonyl, or wherein any carbon atom of said alkyl or alkenyl is optionally replaced with O, NH, NR₂, S, SO, or SO₂;

R₂ is selected from the group consisting of hydrogen, $C_1$–$C_4$ straight or branched chain alkyl, $C_3$–$C_4$ straight or branched chain alkenyl or alkynyl, and $C_1$–$C_4$ bridging alkyl wherein a bridge is formed between the nitrogen and a carbon atom of said alkyl or alkenyl chain containing said heteroatom to form a ring, wherein said ring is optionally fused to an Ar group;

Ar is an alicyclic or aromatic, mono-, bi- or tricyclic, carbo- or heterocyclic ring, wherein the ring is either unsubstituted or substituted with one or more substituent (s); wherein the individual ring size is 5–8 members; wherein the heterocyclic ring contains 1–6 heteroatom(s) independently selected from the group consisting of O, N, and S; wherein an aromatic or tertiary alkyl amine is optionally oxidized to a corresponding N-oxide;

Z is a direct bond, $C_1$–$C_6$ straight or branched chain alkyl, or $C_2$–$C_6$ straight or branched chain alkenyl, wherein any carbon atom of said alkyl or alkenyl is optionally substituted in one or more position(s) with amino, halo, haloalkyl, thiocarbonyl, ester, thioester, alkoxy, alkenoxy, cyano, nitro, imino, alkylamino, aminoalkyl, sulfhydryl, thioalkyl, sulfonyl, or oxygen to form a carbonyl, or wherein any atom of said alkyl or alkenyl is optionally replaced with O, NH, NR₂, S, SO, or SO₂;

R₂ is selected from the group consisting of hydrogen, $C_1$–$C_4$ straight or branched chain alkyl, $C_3$–$C_4$ straight or branched chain alkenyl or alkynyl, and $C_1$–$C_4$ bridging alkyl wherein a bridge is formed between the nitrogen and a carbon atom of said alkyl or alkenyl chain containing said heteroatom to form a ring, wherein said ring is optionally fused to an Ar group;

C and D are independently hydrogen, Ar, $C_1$–$C_6$ straight or branched chain alkyl, or $C_2$–$C_6$ straight or branched chain alkenyl, wherein said alkyl or alkenyl is optionally substituted with one or more substituent(s) independently selected from the group consisting of $C_3$–$C_8$ cycloalkyl, $C_5$–$C_7$ cycloalkenyl, hydroxy, carbonyl oxygen, and Ar; wherein said alkyl, alkenyl, cycloalkyl or cycloalkenyl is optionally substituted with $C_1$–$C_4$ alkyl, $C_2$–$C_4$ alkenyl, or hydroxy; wherein any carbon atom of said alkyl or alkenyl is optionally substituted in one or more position(s) with oxygen to form a carbonyl, or wherein any carbon atom of said alkyl or alkenyl is optionally replaced with O, NH, $NR_2$, S, SO, or $SO_2$; and $R_1$ is selected from the group consisting of Ar, $C_3$–$C_8$ cycloalkyl, $C_1$–$C_6$ straight or branched chain alkyl, and $C_2$–$C_6$ straight or branched chain alkenyl, wherein said alkyl or alkenyl is optionally substituted with one or more substituent(s) independently selected from the group consisting of Ar, $C_3$–$C_8$ cycloalkyl, amino, halo, haloalkyl, hydroxy, trifluoromethyl, $C_1$–$C_6$ straight or branched chain alkyl, $C_2$–$C_6$ straight or branched chain alkenyl, carbonyl, thiocarbonyl, ester, thioester, alkoxy, alkenoxy, cyano, nitro, imino, alkylamino, aminoalkyl, sulfhydryl, thioalkyl, and sulfonyl, wherein any carbon atom of said alkyl or alkenyl is optionally replaced with O, NH, $NR_2$, S, SO, or $SO_2$.

Useful carbo- and heterocyclic rings include without limitation phenyl, benzyl, naphthyl, indenyl, azulenyl, fluorenyl, anthracenyl, indolyl, isoindolyl, indolinyl, benzofuranyl, benzothiophenyl, indazolyl, benzimidazolyl, benzthiazolyl, tetrahydrofuranyl, tetrahydropyranyl, pyridyl, pyrrolyl, pyrrolidinyl, pyridinyl, pyrimidinyl, purinyl, quinolinyl, isoquinolinyl, tetrahydroquinolinyl, quinolizinyl, furyl, thiophenyl, imidazolyl, oxazolyl, benzoxazolyl, thiazolyl, isoxazolyl, isotriazolyl, oxadiazolyl, triazolyl, thiadiazolyl, pyridazinyl, pyrimidinyl, pyrazinyl, triazinyl, trithianyl, indolizinyl, pyrazolyl, pyrazolinyl, pyrazolidinyl, thienyl, tetrahydroisoquinolinyl, cinnolinyl, phthalazinyl, quinazolinyl, quinoxalinyl, naphthyridinyl, pteridinyl, carbazolyl, acridinyl, phenazinyl, phenothiazinyl, and phenoxazinyl.

In a preferred embodiment of formula III, Ar is selected from the group consisting of phenyl, benzyl, naphthyl, indolyl, pyridyl, pyrrolyl, pyrrolidinyl, pyridinyl, pyrimidinyl, purinyl, quinolinyl, isoquinolinyl, furyl, fluorenyl, thiophenyl, imidazolyl, oxazolyl, thiazolyl, pyrazolyl, and thienyl.

In another preferred embodiment of formula III, the N-linked sulfone of heterocyclic thioester is the compound GPI 1312, of the formula

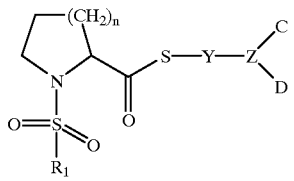

GPI 1312

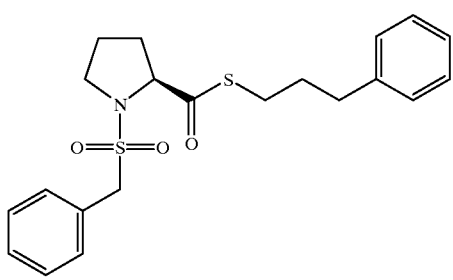

Formula IV

Additionally, the N-linked sulfone of heterocyclic thioester may be a compound of formula IV or a pharmaceutically acceptable salt, ester, or solvate thereof, wherein:

n is 1, 2 or 3;

X is either O or S;

Y is a direct bond, $C_1$–$C_6$ straight or branched chain alkyl, or $C_2$–$C_6$ straight or branched chain alkenyl, wherein any carbon atom of said alkyl or alkenyl is optionally substituted in one or more position(s) with amino, halo, haloalkyl, thiocarbonyl, ester, thioester, alkoxy, alkenoxy, cyano, nitro, imino, alkylamino, aminoalkyl, sulfhydryl, thioalkyl, sulfonyl, or oxygen to form a carbonyl, or wherein any carbon atom of said alkyl or alkenyl is optionally replaced with O, NH, $NR_2$, S, SO, or $SO_2$;

$R_2$ is selected from the group consisting of hydrogen, $C_1$–$C_4$ straight or branched chain alkyl, $C_3$–$C_4$ straight or branched chain alkenyl or alkynyl, and $C_1$–$C_4$ bridging alkyl wherein a bridge is formed between the nitrogen and a carbon atom of said alkyl or alkenyl chain containing said heteroatom to form a ring, wherein said ring is optionally fused to an Ar group;

Z is a direct bond, $C_1$–$C_6$ straight or branched chain alkyl, or $C_2$–$C_6$ straight or branched chain alkenyl, wherein any carbon atom of said alkyl or alkenyl is optionally substituted in one or more position(s) with amino, halo, haloalkyl, thiocarbonyl, ester, thioester, alkoxy, alkenoxy, cyano, nitro, imino, alkylamino, aminoalkyl, sulfhydryl, thioalkyl, sulfonyl, or oxygen to form a carbonyl, or wherein any atom of said alkyl or alkenyl is optionally replaced with O, NH, $NR_2$, S, SO, or $SO_2$;

$R_2$ is selected from the group consisting of hydrogen, $C_1$–$C_4$ straight or branched chain alkyl, $C_3$–$C_4$ straight or branched chain alkenyl or alkynyl, and $C_1$–$C_4$ bridging alkyl wherein a bridge is formed between the nitrogen and a carbon atom of said alkyl or alkenyl chain containing said heteroatom to form a ring, wherein said ring is optionally fused to an Ar group;

Ar is an alicyclic or aromatic, mono-, bi- or tricyclic, carbo- or heterocyclic ring, wherein the ring is either unsubstituted or substituted with one or more substituent(s); wherein the individual ring size is 5–8 members; wherein the heterocyclic ring contains 1–6 heteroatom(s) independently selected from the group consisting of O, N, and S; wherein an aromatic or tertiary alkyl amine is optionally oxidized to a corresponding N-oxide;

C and D are independently hydrogen, Ar, $C_1$–$C_6$ straight or branched chain alkyl, or $C_2$–$C_6$ straight or branched chain alkenyl, wherein said alkyl or alkenyl is optionally substituted with one or more substituent(s) independently selected from the group consisting of $C_3$–$C_8$ cycloalkyl, $C_5$–$C_7$ cycloalkenyl, hydroxy, carbonyl oxygen, and Ar; wherein said alkyl, alkenyl, cycloalkyl or cycloalkenyl is optionally substituted with $C_1$–$C_4$ alkyl, $C_2$–$C_4$ alkenyl, or hydroxy; wherein any carbon atom of said alkyl or alkenyl is optionally substituted in one or more position(s) with oxygen to form a carbonyl, or wherein any carbon atom of said alkyl or alkenyl is optionally replaced with O, NH, $NR_2$, S, SO, or $SO_2$; and R₁ is selected from the group consisting of Ar, $C_3$–$C_8$ cycloalkyl, $C_1$–$C_6$ straight or branched chain alkyl, and $C_2$–$C_6$ straight or branched chain alkenyl, wherein said alkyl or alkenyl is optionally substituted with one or more substituent(s) independently selected from the group consisting of Ar, $C_3$–$C_8$ cycloalkyl, amino, halo, haloalkyl, hydroxy, trifluoromethyl, $C_1$–$C_6$ straight or branched chain alkyl, $C_2$–$C_6$ straight or branched chain alkenyl, carbonyl, thiocarbonyl, ester, thioester, alkoxy, alkenoxy, cyano, nitro, imino, alkylamino, aminoalkyl, sulfhydryl, thioalkyl, and sulfonyl, wherein any carbon atom of said alkyl or alkenyl is optionally replaced with O, NH, $NR_2$, S, SO, or $SO_2$.

Useful carbo- and heterocyclic rings include without limitation phenyl, benzyl, naphthyl, indenyl, azulenyl, fluorenyl, anthracenyl, indolyl, isoindolyl, indolinyl, benzofuranyl, benzothiophenyl, indazolyl, benzimidazolyl, benzthiazolyl, tetrahydrofuranyl, tetrahydropyranyl, pyridyl, pyrrolyl, pyrrolidinyl, pyridinyl, pyrimidinyl, purinyl, quinolinyl, isoquinolinyl, tetrahydroquinolinyl, quinolizinyl, furyl, thiophenyl, imidazolyl, oxazolyl, benzoxazolyl, thiazolyl, isoxazolyl, isotriazolyl, oxadiazolyl, triazolyl, thiadiazolyl, pyridazinyl, pyrimidinyl, pyrazinyl, triazinyl, trithianyl, indolizinyl, pyrazolyl, pyrazolinyl, pyrazolidinyl, thienyl, tetrahydroisoquinolinyl, cinnolinyl, phthalazinyl, quinazolinyl, quinoxalinyl, naphthyridinyl, pteridinyl, carbazolyl, acridinyl, phenazinyl, phenothiazinyl, and phenoxazinyl.

In a preferred embodiment of formula IV, Ar is selected from the group consisting of phenyl, benzyl, naphthyl, indolyl, pyridyl, pyrrolyl, pyrrolidinyl, pyridinyl, pyrimidinyl, purinyl, quinolinyl, isoquinolinyl, furyl, fluorenyl, thiophenyl, imidazolyl, oxazolyl, thiazolyl, pyrazolyl, and thienyl.

Exemplary compounds of formula IV are presented in TABLE I.

TABLE I

| No. | n | Y | Z | C | D | R1 |
|---|---|---|---|---|---|---|
| 1 | 1 | CH₂ | CH | Phenyl | H | Phenyl |
| 2 | 1 | CH₂ | CH | Phenyl | H | α-Methylphenyl |
| 3 | 1 | CH₂ | CH | Phenyl | H | 4-Methylphenyl |
| 4 | 1 | (CH₂)₂ | CH | p-Methoxyphenyl | H | Phenyl |
| 5 | 1 | (CH₂)₂ | CH | p-Methoxyphenyl | H | α-Methylphenyl |
| 6 | 1 | (CH₂)₂ | CH | p-Methoxyphenyl | H | 4-Methylphenyl |
| 7 | 1 | (CH₂)₂ | CH | Phenyl | Phenyl | Phenyl |
| 8 | 1 | (CH₂)₂ | CH | Phenyl | Phenyl | α-Methylphenyl |
| 9 | 1 | (CH₂)₂ | CH | Phenyl | Phenyl | 4-Methylphenyl |
| 10 | 2 | (CH₂)₃ | CH | Phenyl | H | Phenyl |
| 11 | 2 | (CH₂)₃ | CH | Phenyl | H | α-Methylphenyl |
| 12 | 2 | (CH₂)₃ | CH | Phenyl | H | 4-Methylphenyl |
| 13 | 2 | (CH₂)₃ | CH | Phenyl | H | 3,4,5-trimethoxyphenyl |
| 14 | 2 | (CH₂)₃ | CH | Phenyl | H | Cyclohexyl |
| 15 | 2 | Direct bond | CH | 3-Phenylpropyl | 3-Phenylpropyl | Phenyl |
| 16 | 2 | Direct bond | CH | 3-Phenylpropyl | 3-Phenylpropyl | α-Methylphenyl |
| 17 | 2 | Direct bond | CH | 3-Phenylpropyl | 3-Phenylpropyl | 4-Methylphenyl |
| 18 | 2 | Direct bond | CH | 3-Phenylethyl | 3-Phenylethyl | 4-Methylphenyl |
| 19 | 2 | Direct bond | CH | 3-(4-Methoxyphenyl)-propyl | 3-Phenylpropyl | 4-Methylphenyl |
| 20 | 2 | Direct bond | CH | 3-(2-Pyridyl)-propyl | 3-Phenylpropyl | 4-Methylphenyl |

In another preferred embodiment of formula I, the N-linked sulfone of heterocyclic thioester is the compound GPI 1312, of the formula

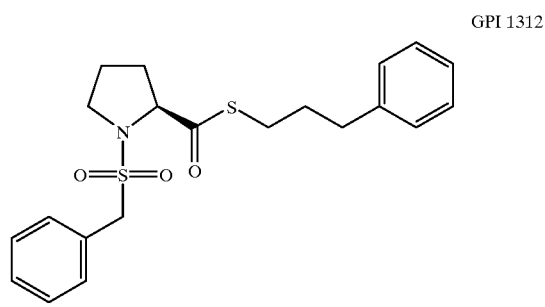

GPI 1312

The most preferred compounds of formula IV are selected from the group consisting of:
3-(para-Methoxyphenyl)-1-propylmercaptyl(2S)-N-(benzenesulfonyl)pyrrolidine-2-carboxylate;

3-(para-Methoxyphenyl)-1-propylmercaptyl(2S)-N-(α-toluenesulfonyl)pyrrolidine-2-carboxylate;

3-(para-Methoxyphenyl)-1-propylmercaptyl(2S)-N-(α-toluenesulfonyl)pyrrolidine-2-carboxylate;

1,5-Diphenyl-3-pentylmercaptyl N-(para-toluenesulfonyl)pipecolate; and pharmaceutically acceptable salts, esters, and solvates thereof.

Formula V

Additionally, the N-linked sulfonamide of a heterocyclic thioester may be a compound of formula V

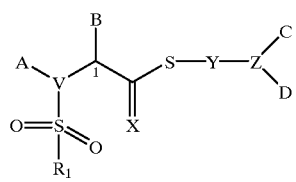

or a pharmaceutically acceptable salt, ester, or solvate thereof, wherein:

V is C, N, or S;

A, B, C, D, $R_1$, X, Y, and Z are as defined in formula I above.

All the compounds of Formulas I–V possess asymmetric centers and thus can be produced as mixtures of stereoisomers or as individual R- and S-stereoisomers. The individual stereoisomers may be obtained by using an optically active starting material, by resolving a racemic or non-racemic mixture of an intermediate at some appropriate stage of the synthesis, or by resolving the compounds of Formulas I–V. It is understood that the compounds of Formulas I–V encompass individual stereoisomers as well as mixtures (racemic and non-racemic) of stereoisomers. Preferably, S-stereoisomers are used in the pharmaceutical compositions and methods of the present invention.

Synthesis of N-linked Sulfone of Heterocyclic Thioester

The compounds of formulas I to V may be readily prepared by standard techniques of organic chemistry, utilizing the general synthetic pathway depicted below. As described by Scheme I, cyclic amino acids protected by suitable blocking groups P on the amino acid nitrogen may be reacted with thiols RSH to generate thioesters 2. After removal of the protecting group, the free amine 3 may be reacted with various sulfonyl chlorides 4 to provide final products in good to excellent yield.

SCHEME I

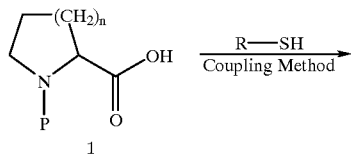

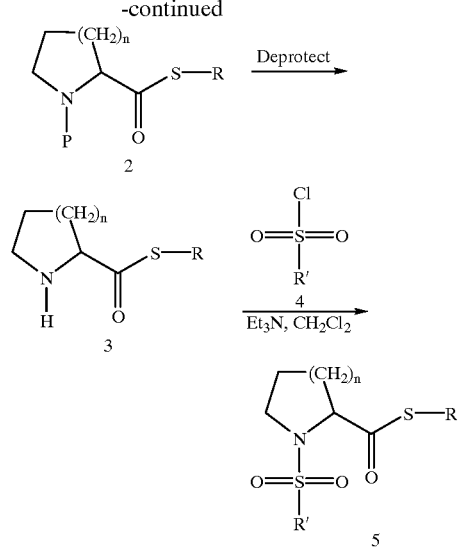

Thiols R-SH may be conveniently prepared from the corresponding readily available alcohols or halides via a two step replacement of halogen by sulfur, as described in Scheme II. Halides may be reacted with thiourea, and the corresponding alkyl thiouronium salts hydrolyzed to provide thiols RSH. If alcohols are used as the starting materials, they may be first converted to the corresponding halides by standard methods.

SCHEME II

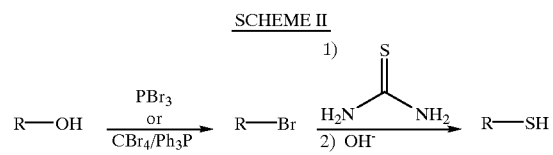

Affinity for FKBP12

The compounds used in the inventive methods and pharmaceutical compositions have an affinity for the FK506 binding protein, particularly FKBP12. The inhibition of the prolyl peptidyl cis-trans isomerase activity of FKBP may be measured as an indicator of this affinity.

$K_i$ Test Procedure

Inhibition of the peptidyl-prolyl isomerase (rotamase) activity of the compounds used in the inventive methods and pharmaceutical compositions can be evaluated by known methods described in the literature (Harding et al., Nature, 1989, 341:758–760; Holt et al. J. Am. Chem. Soc., 115:9923–9938). These values are obtained as apparent $K_i$'s and are presented for representative compounds in TABLE II.

The cis-trans isomerization of an alanine-proline bond in a model substrate, N-succinyl-Ala-Ala-Pro-Phe-p-nitroanilide, is monitored spectrophotometrically in a chymotrypsin-coupled assay, which releases para-nitroanilide from the trans form of the substrate. The inhibition of this reaction caused by the addition of different concentrations of inhibitor is determined, and the data is analyzed as a change in first-order rate constant as a function of inhibitor concentration to yield the apparent $K_i$ values.

In a plastic cuvette are added 950 Ml of ice cold assay buffer (25 mM HEPES, pH 7.8, 100 mM NaCl), 10 mL of FKBP (2.5 mM in 10 mM Tris-Cl pH 7.5, 100 mM NaCl, 1 mM dithiothreitol), 25 mL of chymotrypsin (50 mg/ml in 1 mM HCl) and 10 mL of test compound at various concentrations in dimethyl sulfoxide. The reaction is initiated by the addition of 5 mL of substrate (succinyl-Ala-Phe-Pro-Phe-para-nitroanilide, 5 mg/mL in 2.35 mM LiCl in trifluoroethanol).

The absorbance at 390 nm versus time is monitored for 90 seconds using a spectrophotometer and the rate constants are determined from the absorbance versus time data files.

TABLE II

In Vitro Test Results - Formulas I to V

| Compound | $K_i$ (nM) |
|---|---|
| 1 | +++ |
| 2 | ++ |
| 3 | ++ |
| 4 | ++ |
| 5 | ++ |
| 6 | + |
| 7 | ++ |
| 8 | +++ |
| 9 | +++ |
| 10 | +++ |
| 11 | ++ |
| 12 | +++ |
| 13 | +++ |
| 14 | +++ |
| 15 | +++ |
| 16 | ++ |

Relative potencies of compounds are ranked according to the following scale: ++++ denotes $K_i$ or ED50 < 1 nM; +++ denotes $K_i$ or ED50 of 1–50 nM; ++ denotes $K_i$ or ED 50 of 51–200 nM; + denotes $K_i$ or ED of 201–500 nM.

Route of Administration

To effectively treat alopecia or promote hair growth, the compounds used in the inventive methods and pharmaceutical compositions must readily affect the targeted areas. For these purposes, the compounds are preferably administered topically to the skin.

For topical application to the skin, the compounds can be formulated into suitable ointments containing the compounds suspended or dissolved in, for example, mixtures with one or more of the following: mineral oil, liquid petrolatum, white petrolatum, propylene glycol, polyoxyethylene, polyoxypropylene compound, emulsifying wax and water. Alternatively, the compounds can be formulated into suitable lotions or creams containing the active compound suspended or dissolved in, for example, a mixture of one or more of the following: mineral oil, sorbitan monostearate, polysorbate 60, cetyl ester wax, cetearyl alcohol, 2-octyldodecanol, benzyl alcohol and water.

Other routes of administration known in the pharmaceutical art are also contemplated by this invention.

Dosage

Dosage levels on the order of about 0.1 mg to about 10,000 mg of the active ingredient compound are useful in the treatment of the above conditions, with preferred levels of about 0.1 mg to about 1,000 mg. The specific dose level for any particular patient will vary depending upon a variety of factors, including the activity of the specific compound employed; the age, body weight, general health, sex and diet of the patient; the time of administration; the rate of excretion; drug combination; the severity of the particular disease being treated; and the form of administration. Typically, in vitro dosage-effect results provide useful guidance on the proper doses for patient administration. Studies in animal models are also helpful. The considerations for determining the proper dose levels are well known in the art.

The compounds can be administered with other hair revitalizing agents. Specific dose levels for the other hair revitalizing agents will depend upon the factors previously stated and the effectiveness of the drug combination.

EXAMPLES

The following examples are illustrative of the present invention and are not intended to be limitations thereon. Unless otherwise indicated, all percentages are based upon 100% by weight of the final composition.

Example 1

Synthesis of 3-(para-Methoxyphenyl)-1-propylmercaptyl(2S)-N-(benzenesulfonyl) pyrrolidine-2-carboxylate (4)

3-(p-Methoxyphenyl)-1-propylbromide

To a solution of 3-(p-methoxyphenyl)-1-propanol (16.6 g; 0.1 mol) in 250 mL of toluene, cooled to 0° C., was added dropwise 26 mL of phosphorus tribromide (0.27 mol). Following completion of the addition, the reaction was stirred at room temperature for 1 hour, then refluxed for an additional hour. The reaction was cooled and poured onto ice, the layers were separated, and the organic phase washed with saturated sodium bicarbonate (3×) and brine (3×). The crude material obtained upon drying and evaporation of the solvent was chromatographed, eluting with 10% EtOAc/hexane, to obtain 14 g (61%) of 3-(p-methoxyphenyl)-1-propylbromide. 3-(p-Methoxyphenyl)-1-propylmercaptan A mixture of 3-(p-methoxyphenyl)-1-propylbromide (14 g; 61 mmol) and thiourea (5.1 g; 67 mmol) in ethanol (150 mL) was refluxed for 48 hours. Evaporation of the solvent provided a clear glassy compound, which was dissolved in 50 mL of water and treated with 100 mL of 40% aqueous sodium hydroxide. After stirring the resulting mixture for two hours, the product was extracted into ether (3×), and the combined organic extracts were washed with sodium bicarbonate and brine, dried, and concentrated. Chromatographic purification of the crude thiol on a silica gel column eluting with 2-either in hexane delivered 10.2 g of 3-(p-methoxyphenyl)- 1-propylmercaptan as a clear liquid. $^1$H NMR (300 MHz, CDCl$_3$): δ 1.34 (t, 1H); 1.88–1.92 (m, 2H); 2.49–2.53 (m, 2H); 2.64–2.69 (m, 2H); 3.77 (s, 3H); 6.80–6.84 (m, 2H); 7.06–7.24 (m, 2H).

3-(p-Methoxyphenyl)-1-mercaptyl N-(tert-butyloxycarbonyl)pyrrolidine-2-carboxylate A mixture of N-(tert-butyloxycarbonyl)-(S)-proline (2.0 g; 9.29 mmol), 3-(p-methoxyphenyl)-1-propylmercaptan (1.86 g; 10.22 mmol), 1-(3-dimethylaminopropyl)-3-ethylcarbodiimide hydrochloride (1.96 g; 10.22 mmol), and 4-dimethylaminopyridine (catalytic) in dry methylene chloride (50 mL) was stirred overnight. The reaction mixture was diluted with methylene chloride (50 mL) and water 100 (mL), and the layers were separated. The organic phase was washed with water (3×100 mL), dried over magnesium sulfate, and concentrated to provide 3.05 g of the product (100%) as a thick oil. $^1$H NMR (300 MHz, CDCl$_3$): δ 1.15 (s, 9H); 1.84–2.31 (m, 6H); 2.61 (m, 2H); 2.83 (m, 2H); 3.51 (m, 2H); 3.75 (s, 3H); 6.79 (d, 2H, J=8.04); 7.05 (m, 2H).

3-(p-Methoxyohenyl)-1-mercaptyl pyrrolidine-2-carboxylate

A solution of 3-(p-methoxyphenyl)-mercaptyl N-(tert-butyloxycarbonyl)pyrrolidine-2-carboxylate (3.0 g; 8.94 mmol) in methylene chloride (60 mL) and trifluoroacetic acid (6 mL) was stirred at room temperature for three hours. Saturated potassium carbonate was added until the pH was basic, and the reaction mixture was extracted with methylene chloride (3×). The combined organic extracts were dried and concentrated to yield 1.73 g (69.) of the free amine as a thick oil. $^1$H NMR (300 MHz, CDCl$_3$) δ 1.80–2.23 (m, 6H); 2.62 (m, 2H); 2.81 (m, 2H); 3.01 (m, 2H); 3.75 (s, 3H); 3.89(m, 1H); 6.81 (m, 2H); 7.06 (m, 2H).

3-(para-Methoxyphenyl)-1-propylmercaptyl (2S)-N-(benzenesulfonyl)pyrrolidine-2-carboxylate (4)

A solution of 3-(p-methoxyphenyl)-1-mercaptyl pyrrolidine-2-carboxylate (567 mg; 2.03 mmol) and benzenesulfonyl chloride (358 mg; 2.03 mmol) in methylene chloride (5 mL) was treated with diisopropylethylamine (290 mg; 2.23 mmol) and stirred overnight at room temperature. The reaction mixture was filtered to remove solids and applied directly to a silica gel column, eluting with 25-ethyl acetate in hexane, to obtain 540 mg of Compound 4 (Table I) as a clear oil. $^1$H NMR (300 MHz, CDCl$_3$) δ 1.65–1.89 (m, 6H); 2.61 (t, 2H, J=7.3); 2.87 (t, 2H, J=7.6); 3.26 (m, 1H); 3.54 (m, 1H); 3.76 (s, 3H); 4.34 (dd, 1H, J=2.7, 8.6); 6.79 (d, 2H, J=8.7); 7.06 (d, 2H, J=8.6); 7.49–7.59 (m, 3H); 7.86 (dd, 2H, J=1.5, 6.8).

Example 2

Synthesis of 3-(para-Methoxyphenyl)-1-propylmercaptyl(2S)-N-(α-toluenesulfonyl) pyrrolidine-2-carboxylate (5)

A solution of 3-(p-Methoxyphenyl)-1-mercaptyl pyrrolidine-2-carboxylate (645 mg; 2.30 mmol) and α-toluenesulfonyl chloride (440 mg; 2.30 mmol) in methylene chloride (5 mL) was treated with diisopropylethylamine (330 mg; 2.53 mmol) and stirred overnight at room temperature. Purification as described for Example 1 provided the compound of Example 2 (Compound 5, Table I) as a clear oil. $^1$H NMR (300 MHz, CDCl$_3$) δ 1.65–2.25 (m, 8H); 2.65 (t, 2H); 2.89–2.96 (m, 2H); 3.55–3.73 (m, 2H); 3.80 (s, 3H); 4.32 (s, 2H); 4.70–4.81 (m, 1H); 6.83 (d, 2H); 7.09 (d, 2H); 7.14 (m, 3H); 7.26 (m, 2H).

Example 3

Synthesis of 3-(para-Methoxyphenyl)-1-propylmercaptyl(2S)-N-(α-toluenesulfonyl) pyrrolidine-2-carboxylate (6)

A solution of 3-(p-methoxyphenyl)-1-mercaptyl pyrrolidine-2-carboxylate (567 mg; 2.30 mmol) and p-toluenesulfonyl chloride (425 mg; 2.23 mmol) in methylene chloride (5 mL) was stirred overnight at room temperature. Purification as described for Example 1 provided the compound of Example 3 (Compound 6, Table I) as a clear oil. $^1$H NMR (300 MHz, CDCl$_3$): δ 1.67–1.94 (m, 6H); 2.40 (s, 3H); 2.61 (t, 2H, J=7.3); 2.84 (m, 2H, J=7.2); 3.22 (m, 1H); 3.52 (m, 1H); 3.76 (s, 3H); 4.32 (dd, 1H, J=2.9, 8.5); 6.79 (d, 2H, J=6.5); 7.07 (d, 2H, J=6.5); 7.29 (d, 2H, J=6.5); 7.74 (d, 2H, J=6.5).

Example 4

Synthesis of 1.5-Diphenyl-3-pentylmercaptyl N-(para-toluenesulfonyl)pipecolate (18)

3-Phenyl-1-propanal

Oxalyl chloride (2.90 g; 2.29 mmol) in methylene chloride (50 mL), cooled to −78° C., was treated with dimethylsulfoxide (3.4 mL) in 10 mL of methylene chloride. After stirring for 5 min, 3-phenyl-1-propanol (2.72 g; 20 mmol) in 20 mL of methylene chloride was added, and the resulting mixture was stirred at −78° C. for 15 min, treated with 14 mL of triethylamine, stirred an additional 15 min, and poured into 100 mL of water. The layers were separated, the organic phase was dried and concentrated, and the crude residue was purified on a silica gel column, eluting with 10% ethyl acetate in hexane, to obtain 1.27 g (47%) of the aldehyde as a clear oil. $^1$H NMR (300 MHz, CDCl$_3$): δ 2.80 (m, 2H); 2.98 (m, 2H); 7.27 (m, 5H); 9.81 (2, 1H).

1,5-Diphenyl-3—pentanol

A solution of 2-(bromoethyl)benzene (1.73 g; 9.33 mmol) in diethylether (10 mL) was added to a stirred slurry of magnesium turnings (250 mg; 10.18 mmol) in 5 mL of ether. The reaction was initiated with a heat gun, and after the addition was complete the mixture was heated on an oil bath for 30 min. 3-Phenyl-1-propanal (1.25 g; 9.33 mmol) was added in 10 mL of ether, and reflux was continued for 1 hour. The reaction was cooled and quenched with saturated ammonium chloride, extracted into 2× ethyl acetate, and the combined organic portions were dried and concentrated. Chromatographic purification on a silica gel column (10% ethyl acetate in hexane) delivered 1.42 g(63%) of the diphenyl alcohol. $^1$H NMR (300 MHz, CDCl$_3$): δ 1.84 (m, 4H); 2.61–2.76(m, 4H); 3.65 (m, 1H); 7.19–7.29 (m, 1H).

1,5-Diphenyl-3-bromopentane

To a solution of 1,5-diphenyl-3-pentanol (1.20 g (5 mmol) and carbon tetrabromide (1.67 g; 5 mmol) in methylene chloride (20 mL) was added triphenylphosphine (1.31 g; 5 mmol) portionwise, at 0° C. After stirring at room temperature for 18 hours, the mixture was concentrated, triturated with ether, and the solids removed by filtration. The filtrate was passed through a plug of silica gel, eluting with hexane:methylene chloride, 10:1, to give 1.35 g (90%) of the bromide as an oil which was used without further purification. $^1$H NMR (300 MHz, CDCl$_3$): δ 2.11–2.18 (m, 4H); 2.73 (m, 2H); 2.86 (m, 2H); 3.95 (m, 1H); 7.16–7.30 (m, 10H).

1,5-Diphenyl-3-pentylmercaptan

Using the procedure described in Example 10 for the conversion of bromides to thiols, 1,5-diphenyl-3-bromopentane was converted to 1,5-diphenyl-3-pentylmercaptan in 35% overall yield. $^1$H NMR (300 MHz, CDCl$_3$): δ 1.79 (m, 2H); 1.98 (m, 2H); 2.71 (m, 3H); 2.80 (m, 2H); 7.16–7.28 (m, 10H).

1,5-Diphenyl-3-pentylmercaptyl N-(tert-butyloxycarbonyl) pyrrolidine-2-carboxylate A mixture of N-(tert-butyloxycarbonyl)-(S)-pipecolic acid (2.11 g; 9.29 mmol), 1,5-diphenyl-3-pentylmercaptan (2.58 g; 10.22 mmol), 1-(3-dimethylaminopropyl)-3-ethylcarbodiimide hydrochloride (1.96 g; 10.22 mmol) and 4-dimethylaminopyridine (catalytic) in dry methylene chloride (50 mL) was stirred overnight. the reaction mixture was diluted with methylene chloride (50 mL) and water (100 mL), and the layers were separated. The organic phase was washed with water (3×100 mL), dried over magnesium sulfate, and concentrated to provide 870 mg (20%) of the product as a thick oil, which was used without further purification.

1,5-Diphenyl-3-pentylmercaptyl pyrrolidine-2-carboxylate

A solution of 1,5-diphenyl-3-pentylmercaptyl N-(tert-butyloxycarbonyl)pyrrolidine-2-carboxylate (850 mg; 1.8 mmol) in methylene chloride (10 mL) and trifluoroacetic acid (1 mL) was stirred at room temperature for three hours. Saturated potassium carbonate was added until the pH was basic, and the reaction mixture was extracted with methylene chloride. The combined organic extracts were dried and concentrated to yield 480 mg (72%) of the free amine as a thick oil, which was used without further purification.

1,5-Diphenyl-3-pentylmercaptyl N-(para-toluenesulfonyl)pipecolate (18)

1,5-Diphenyl-3-pentylmercaptyl N-(para-toluenesulfonyl)pipecolate (18) was prepared from 1,5-diphenyl-3-pentylmercaptyl pyrrolidine-2-carboxylate and para-toluenesulfonyl chloride as described for Example 3, in 65% yield. $^1$H NMR (CDCl$_3$, 300 MHz): δ 0.80 (m, 4H); 1.23–1.97 (m, 5H); 2.15 (d, 1H); 2.61–2.69 (m, 4H); 3.23 (m, 1H); 3.44 (dm, 1H); 4.27 (s, 2H); 4.53 (d, 1H, J=4.5); 5.06 (m, 1H); 7.16–7.34 (m, 15H).

Example 5

In Vivo Hair Generation Tests With C57 Black 6 Mice

Figure 2:
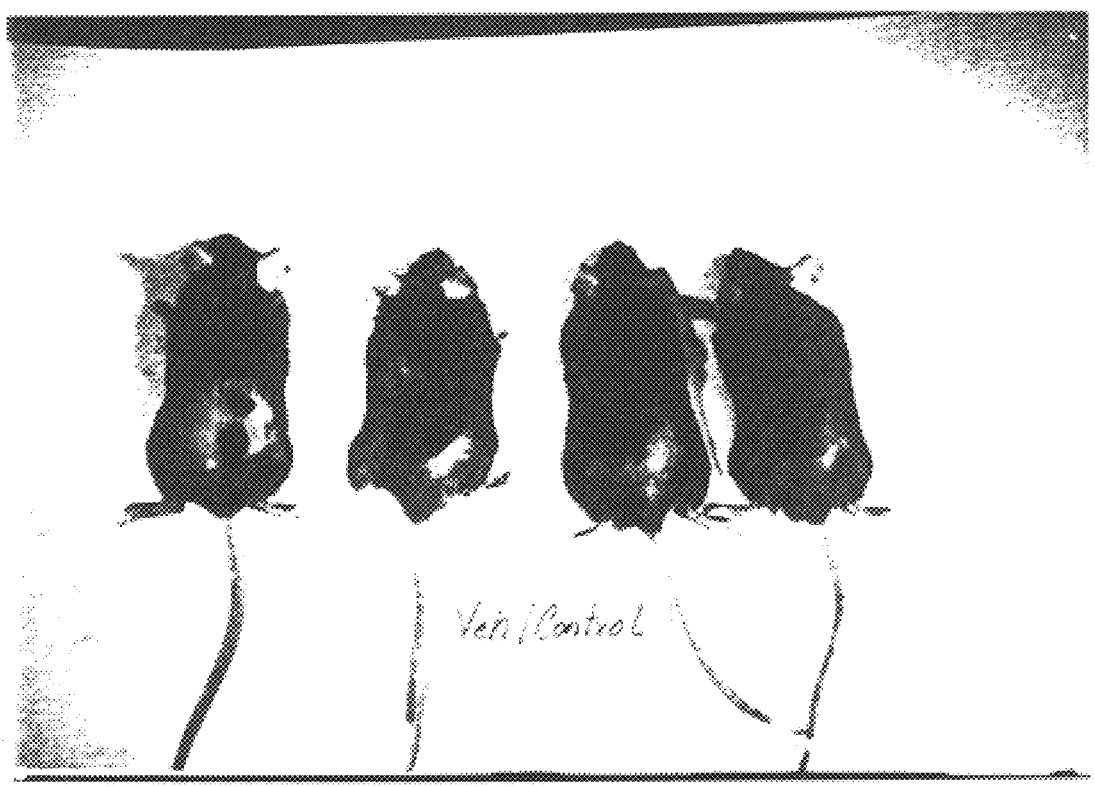
FIG. 2 is a photograph of mice treated with a vehicle after six weeks.
Figure 3:
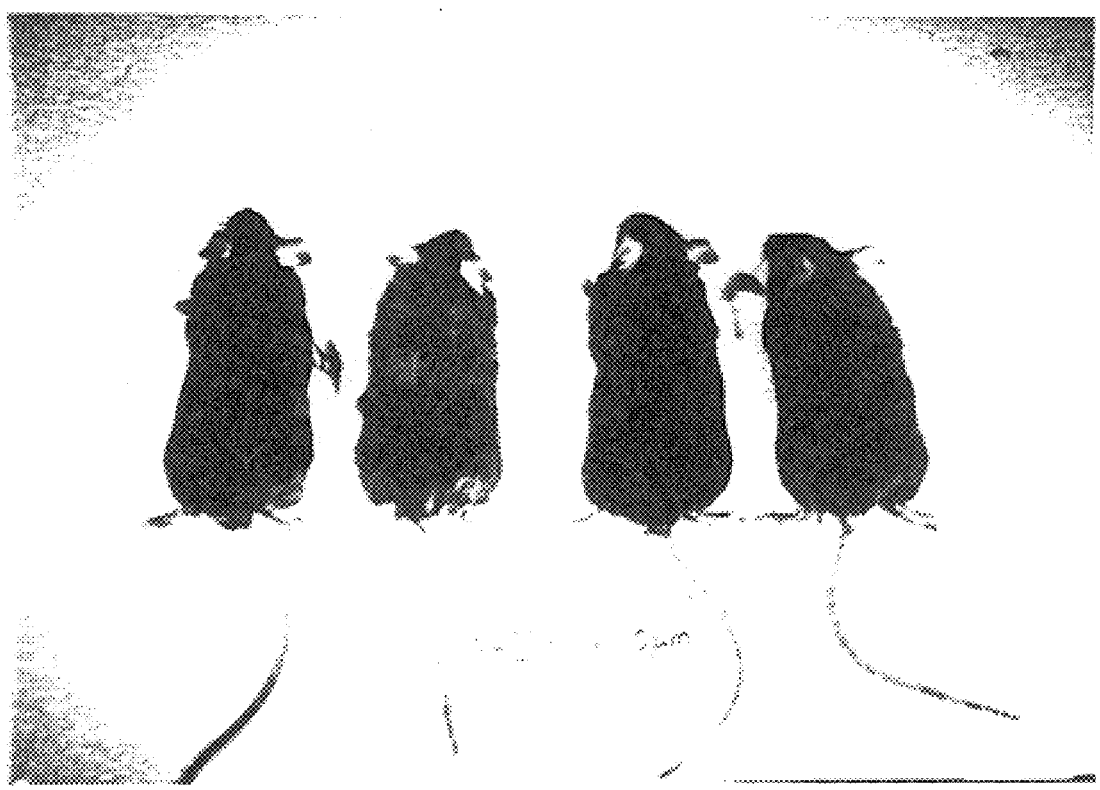
FIG. 3 is a photograph of mice treated with 10 $\mu$M of GPI 1046, a related non-immunosuppressive neuro-immunophillin FKBP ligand, after six weeks.
Figure 4:
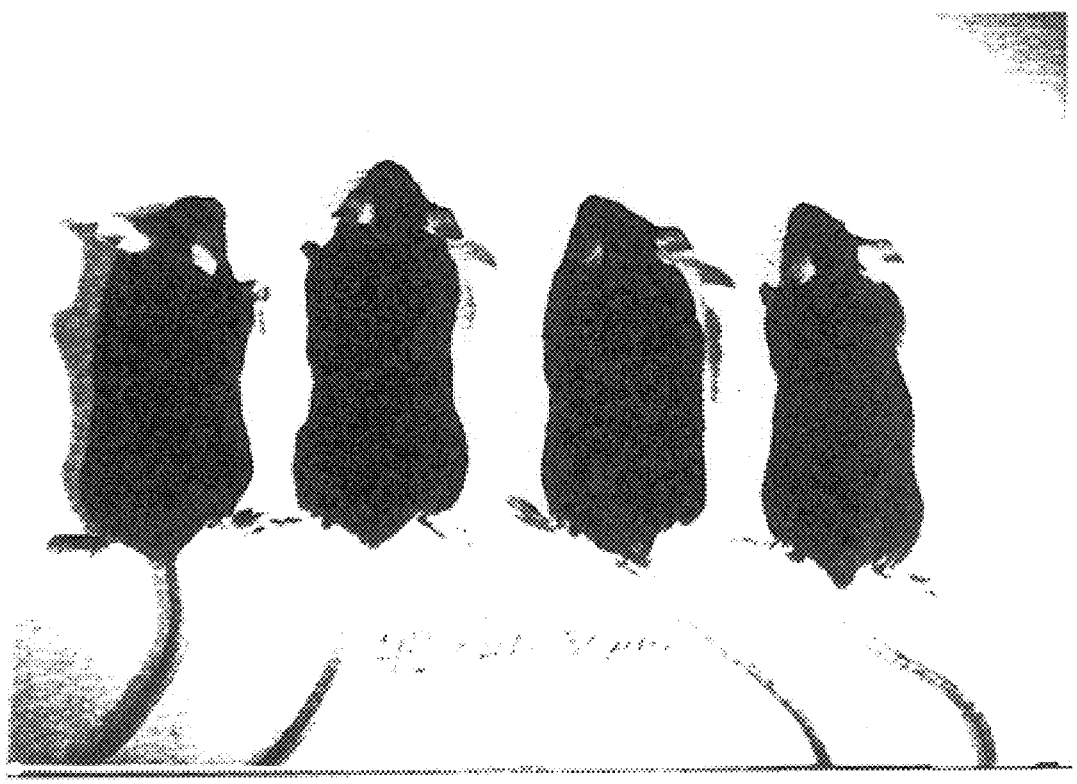
FIG. 4 is a photograph of mice treated with 30 $\mu$M of GPI 1046, a related non-immunosuppressive neuro-immunophillin FKBP ligand, after six weeks.

Experiment A: C57 black 6 mice were used to demonstrate the hair revitalizing properties of a low molecular weight, small molecule, neuro-immunophilin FKBP ligand, GPI 1046, which is related to N-linked sulfones of heterocyclic thioesters. Referring now to FIGS. 1 and 2 of the drawings, C57 black 6 mice, approximately 7 weeks old, had an area of about 2 inches by 2 inches on their hindquarters shaved to remove all existing hair. Care was taken not to nick or cause abrasion to the underlaying dermal layers. The animals were in anagen growth phase, as indicated by the pinkish color of the skin. Referring now to FIGS. 2, 3 and 4, four animals per group were treated by topical administration with 20% propylene glycol vehicle (FIG. 2), 10 μM GPI 1046 (FIG. 3) or 30 μM GPI 1046 (FIG. 4) dissolved in the vehicle. The animals were treated with vehicle or GPI 1046 every 48 hours (3 applications total over the course of 5 days) and the hair growth was allowed to proceed for 6 weeks. Hair growth was quantitated by the percent of shaved area covered by new hair growth during this time period.

FIG. 2 shows that animals treated with vehicle exhibited only a small amount of hair growth in patches or tufts, with less than 3% of the shaved area covered with new growth. In contrast, FIG. 3 shows that animals treated with 10 μM GPI 1046 exhibited dramatic hair growth, covering greater than 90% of the shaved area in all animals. Further, FIG. 4 shows that mice treated with 30 μM GPI 1046 exhibited essentially complete hair regrowth and their shaved areas were indistinguishable from unshaven C57 black 6 mice.

Experiment B: C57 Black 6 mice were used to demonstrate the hair revitalizing properties of various low molecular weight, small molecule, non-immunosuppressive neuroimmunophilin FKBP ligands, including GPI 1312. C57 Black 6 mice, 55 to 75 days old, had an area of about 2 inches by 2 inches on their hindquarters shaved to remove all existing hair. Care was taken not to nick or cause abrasion to the underlying dermal layers. The animals were in anagen growth phase when shaved. Five animals per group were treated by topical administration with a vehicle, FK506, or one of the low molecular weight, small molecule, non-immunosuppressive neuroimmunophilin FKBP ligands (GPI 1605, 1046, 1312, 1572, 1389, 1511, and 1234) at a concentration of one micromole per milliliter to the shaved area. The animals were treated three times per week, and hair growth was evaluated 14 days after initiation of treatment. Hair growth was quantitated by the percent of shaved area covered by new hair growth, as scored by a blinded observer, on a scale of 0 (no growth) to five (complete hair regrowth in shaved area).

FIG. 5 shows that after 14 days, the animals treated with vehicle exhibited the beginning of growth in small tufts. In contrast, animals treated with one of the low molecular weight, small molecule, non-immunosuppressive neuroimmunophilin FKBP ligands, including GPI 1312, exhibited dramatic hair growth.

Example 6

A lotion comprising the following composition may be prepared.

|  | (%) |
| --- | --- |
| 95% Ethanol | 80.0 |
| an N-linked sulfonamide of a heterocyclic thioester as defined above | 10.0 |
| α-Tocopherol acetate | 0.01 |
| Ethylene oxide (40 mole) adducts of hardened castor oil | 0.5 |
| purified water | 9.0 |
| perfume and dye | q.s. |

Into 95% ethanol are added an N-linked sulfone of heterocyclic thioester α-tocopherol acetate, ethylene oxide (40 mole) adducts of hardened castor oil, perfume and a dye. The resulting mixture is stirred and dissolved, and purified water is added to the mixture to obtain a transparent liquid lotion.

5 ml of the lotion may be applied once or twice per day to a site having marked baldness or alopecia.

Example 7

A lotion comprising the following composition shown may be prepared.

|  | (%) |
| --- | --- |
| 95% Ethanol | 80.0 |
| an N-linked sulfonamide of a heterocyclic thioester as defined above | 0.005 |
| Hinokitol | 0.01 |
| Ethylene oxide (40 mole) adducts of hardened castor oil | 0.5 |
| Purified water | 19.0 |
| Perfume and dye | q.s. |

Into 95% ethanol are added an N-linked sulfone of heterocyclic thioester, hinokitol, ethylene oxide (40 mole) adducts of hardened castor oil, perfume, and a dye. The resulting mixture is stirred, and purified water is added to the mixture to obtain a transparent liquid lotion.

The lotion may be applied by spraying once to 4 times per day to a site having marked baldness or alopecia.

Example 8

An emulsion may be prepared from A phase and B phase having the following compositions.

|  | (%) |
| --- | --- |
| (A phase) | |
| Whale wax | 0.5 |
| Cetanol | 2.0 |
| Petrolatum | 5.0 |
| Squalene | 10.0 |
| Polyoxyethylene (10 mole) monostearate | 2.0 |

|  | (%) |
| --- | --- |
| Sorbitan monooleate | 1.0 |
| an N-linked sulfonamide of a heterocyclic thioester as defined above | 0.01 |
| (B phase) | |
| Glycerine | 10.0 |
| Purified water | 69.0 |
| Perfume, dye, and preservative | q.s. |

The A phase and the B phase are respectively heated and melted and maintained at 80° C. Both phases are then mixed and cooled under stirring to normal temperature to obtain an emulsion.

The emulsion may be applied by spraying once to four times per day to a site having marked baldness or alopecia.

Example 9

A cream may be prepared from A phase and B phase having the following compositions.

|  | (%) |
| --- | --- |
| (A Phase) | |
| Fluid paraffin | 5.0 |
| Cetostearyl alcohol | 5.5 |
| Petrolatum | 5.5 |
| Glycerine monostearate | 33.0 |
| Polyoxyethylene (20 mole) 2-octyldodecyl ether | 3.0 |
| Propylparaben | 0.3 |
| (B Phase) | |
| an N-linked sulfonamide of a heterocyclic thioester as defined above | 0.8 |
| Glycerine | 7.0 |
| Dipropylene glycol | 20.0 |
| Polyethylene glycol 4000 | 5.0 |
| Sodium Hexametaphosphate | 0.005 |
| Purified water | 44.895 |

The A phase is heated and melted, and maintained at 70° C. The B phase is added into the A phase and the mixture is stirred to obtain an emulsion. The emulsion is then cooled to obtain a cream.

The cream may be applied once to 4 times per day to a site having marked baldness or alopecia.

Example 10

|  | (%) |
| --- | --- |
| Polyoxyethylene butyl ether | 20.0 |
| Ethanol | 50.0 |
| an N-linked sulfonamide of a heterocyclic thioester as defined above | 0.001 |
| Propylene glycol | 5.0 |
| Polyoxyethylene hardened castor oil derivative (ethylene oxide 80 mole adducts) | 0.4 |
| Perfume | q.s. |
| Purified water | q.s. |

Into ethanol are added polyoxypropylene butyl ether, propylene glycol, polyoxyethylene hardened castor oil, an N-linked sulfone of heterocyclic thioester, and perfume. The resulting mixture is stirred, and purified water is added to the mixture to obtain a liquid.

The liquid may be applied once to 4 times per day to a site having marked baldness or alopecia.

Example 11

A shampoo comprising the following composition may be prepared.

|  | (%) |
| --- | --- |
| Sodium laurylsulfate | 5.0 |
| Triethanolamine laurylsulfate | 5.0 |
| Betaine lauryldimethylaminoacetate | 6.0 |
| Ethylene glycol distearate | 2.0 |
| Polyethylene glycol | 5.0 |
| an N-linked sulfonamide of a heterocyclic thioester as defined above | 5.0 |
| Ethanol | 2.0 |
| Perfume | 0.3 |
| Purified water | 69.7 |

Into 69.7 of purified water are added 5.0 g of sodium laurylsulfate, 5.0 g of triethanolamine laurylsulfate, 6.0 g of betaine lauryldimethylaminoacetate. Then a mixture obtained by adding 5.0 g of an N-linked sulfone of heterocyclic thioester, 5.0 g of polyethylene glycol, and 2.0 g of ethylene glycol distearate to 2.0 g of ethanol, followed by stirring, and 0.3 g of perfume are successively added. The resulting mixture is heated and subsequently cooled to obtain a shampoo.

The shampoo may be used on the scalp once or twice per day.

Example 12

A patient is suffering from alopecia senilis. An N-linked sulfone of heterocyclic thioester as identified above, or a pharmaceutical composition comprising the same, may be administered to the patient. Increased hair growth is expected to occur following treatment.

Example 13

A patient is suffering from male pattern alopecia. An N-linked sulfone of heterocyclic thioester as identified above, or a pharmaceutical composition comprising the same, may be administered to the patient. Increased hair growth is expected to occur following treatment.

Example 14

A patient is suffering from alopecia areata. An N-linked sulfone of heterocyclic thioester as identified above, or a pharmaceutical composition comprising the same, may be administered to the patient. Increased hair growth is expected to occur following treatment.

Example 15

A patient is suffering from hair loss caused by skin lesions. An N-linked sulfone of heterocyclic thioester as identified above, or a pharmaceutical composition comprising the same, may be administered to the patient. Increased hair growth is expected to occur following treatment.

Example 16

A patient is suffering from hair loss caused by tumors. An N-linked sulfone of heterocyclic thioester as identified above, or a pharmaceutical composition comprising the same, may be administered to the patient. Increased hair growth is expected to occur following treatment.

Example 17

A patient is suffering from hair loss caused by a systematic disorder, such as a nutritional disorder or an internal secretion disorder. An N-linked sulfone of heterocyclic thioester as identified above, or a pharmaceutical composition comprising the same, may be administered to the patient. Increased hair growth is expected to occur following treatment.

Example 18

A patient is suffering from hair loss caused by chemotherapy. An N-linked sulfone of heterocyclic thioester as identified above, or a pharmaceutical composition comprising the same, may be administered to the patient. Increased hair growth is expected to occur following treatment.

Example 19

A patient is suffering from hair loss caused by radiation. An N-linked sulfone of heterocyclic thioester as identified above, or a pharmaceutical composition comprising the same, may be administered to the patient. Increased hair growth is expected to occur following treatment.

The invention being thus described, it will be obvious that the same may be varied in many ways. Such variations are not to be regarded as a departure from the spirit and scope of the invention and all such modifications are intended to be included within the scope of the following claims.

We claim:

1. A pharmaceutical composition which comprises:
   (i) an effective amount of an N-linked sulfone of a heterocyclic thioester compound for treating alopecia or promoting hair growth in an animal;
   (ii) a alopecia treating or hair growth promoting compound second hair revitalizing agent; and
   (iii) a pharmaceutically acceptable carrier.

2. The pharmaceutical composition of claim 1, wherein the compound is non-immunosuppressive.

3. The pharmaceutical composition of claim 1, wherein the compound has an affinity for an FKBP-type immunophilin.

4. The pharmaceutical composition of claim 3, wherein the FKBP-type immunophilin is FKBP-12.

5. The pharmaceutical composition of claim 1, wherein the compound is of formula I

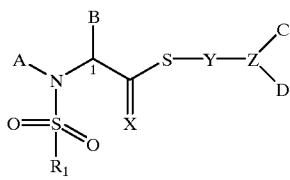

I or a pharmaceutically acceptable salt, ester, or solvate thereof, wherein:

A and B, taken together with the nitrogen and carbon atoms to which they are respectively attached, form a 5–7 membered saturated or unsaturated heterocyclic ring comprising one or more O, S, SO, $SO_2$, N, or $NR_2$ heteroatom(s);

X is either O or S;

Y is a direct bond, $C_1$–$C_6$ straight or branched chain alkyl, or $C_2$–$C_6$ straight or branched chain alkenyl, wherein any carbon atom of said alkyl or alkenyl is optionally substituted in one or more position(s) with amino, halo, haloalkyl, thiocarbonyl, ester, thioester, alkoxy, alkenoxy, cyano, nitro, imino, alkylamino, aminoalkyl, sulfhydryl, thioalkyl, sulfonyl, or oxygen to form a carbonyl, or wherein any carbon atom of said alkyl or alkenyl is optionally replaced with O, $NR_2$, S, SO, or $SO_2$;

$R_2$ is selected from the group consisting of hydrogen, $C_1$–$C_4$ straight or branched chain alkyl, $C_3$–$C_4$ straight or branched chain alkenyl or alkynyl, and $C_1$–$C_4$ bridging alkyl, wherein a bridge is formed between the nitrogen and a carbon atom of said alkyl or alkenyl chain having said heteroatom to form a ring, wherein said ring is optionally fused to an Ar group;

Ar is an alicyclic or aromatic, mono-, bi- or tricyclic, carbo- or heterocyclic ring, wherein the ring is either unsubstituted or substituted with one or more substituent(s);

wherein the individual ring size is 5–8 members;

wherein the heterocyclic ring has 1–6 heteroatom(s) independently selected from the group consisting of O, N, and S, wherein an aromatic or tertiary alkyl amine is optionally oxidized to a corresponding N-oxide;

Z is a direct bond, $C_1$–$C_6$ straight or branched chain alkyl, or $C_2$–$C_6$ straight or branched chain alkenyl, wherein any carbon atom of said alkyl or alkenyl is optionally substituted in one or more position(s) with amino, halo, haloalkyl, thiocarbonyl, ester, thioester, alkoxy, alkenoxy, cyano, nitro, imino, alkylamino, aminoalkyl, sulfhydryl, thioalkyl, sulfonyl, or oxygen to form a carbonyl, or wherein any atom of said alkyl or alkenyl is optionally replaced with O, $NR_2$, S, SO, or $SO_2$;

C and D are independently hydrogen, Ar, $C_1$–$C_6$ straight or branched chain alkyl, or $C_2$–$C_6$ straight or branched chain alkenyl;

wherein said alkyl or alkenyl is optionally substituted with one or more substituent(s) independently selected from the group consisting of $C_3$–$C_8$ cycloalkyl, $C_5$–$C_7$ cycloalkenyl, Oxygen to form a carbonyl, Ar, $C_1$–$C_6$ alkyl, $C_2$–$C_6$ alkenyl, hydroxy, amino, halo, haloalkyl, thiocarbonyl, ester, thioester, alkoxy, alkenoxy, cyano, nitro, imino, alkylamino, aminoalkyl, sulfhydryl, thioalkyl, and sulfonyl, wherein said cycloalkyl or cycloalkenyl is optionally substituted with $C_1$–$C_6$ alkyl, $C_2$–$C_6$ alkenyl, hydroxy, amino, halo, haloalkyl, thiocarbonyl, ester, thioester, alkoxy, alkenoxy, cyano, nitro, imino, alkylamino, aminoalkyl, sulfhydryl, thioalkyl, or sulfonyl, or wherein any carbon atom of said alkyl or alkenyl is optionally replaced with O, $NR_2$, S, SO, or $SO_2$; and $R_1$ is selected from the group consisting of Ar, $C_3$–$C_8$ cycloalkyl, $C_1$–$C_6$ straight or branched chain alkyl, and $C_2$–$C_6$ straight or branched chain alkenyl, wherein said alkyl or alkenyl is optionally substituted with one or more substituent(s) independently selected from the group consisting of Ar, $C_3$–$C_8$ cycloalkyl, amino, halo, haloalkyl, hydroxy, trifluoromethyl, $C_1$–$C_6$ straight or branched chain alkyl, $C_2$–$C_6$ straight or branched chain alkenyl, carbonyl, thiocarbonyl, ester, thioester, alkoxy, alkenoxy, cyano, nitro, imino, alkylamino, aminoalkyl, sulfhydryl, thioalkyl, and sulfonyl;

wherein any carbon atom of said alkyl or alkenyl is optionally replaced with O, $NR_2$, S, SO, or $SO_2$.

6. The pharmaceutical composition of claim 5, wherein the mono- or bicyclic, carbo- or heterocyclic ring is selected from the group consisting of phenyl, benzyl, naphthyl, indolyl, pyridyl, pyrrolyl, pyrrolidinyl, pyridinyl, pyrimidinyl, purinyl, quinolinyl, isoquinolinyl, furyl, fluorenyl, thiophenyl, imidazolyl, oxazolyl, thiazolyl, pyrazolyl, and thienyl.

7. The pharmaceutical composition of claim 6, wherein:
A and B are taken together, with the nitrogen and carbon atoms to which they are respectively attached, to form a 6 membered saturated or unsaturated heterocyclic ring; and
$R_2$ is $C_4$–$C_7$ branched chain alkyl, $C_4$–$C_7$ cycloalkyl, phenyl, or 3,4,5-trimethoxyphenyl.

8. The pharmaceutical composition of claim 5, wherein the compound is selected from the group consisting of:
3-phenylpropyl(2S)-N-(benzylsulfonyl)pyrrolidine-2-carboxythioate;
3-(para-Methoxyphenyl)-1-propylmercaptyl(2S)-N-(benzenesulfonyl)pyrrolidine-2-carboxylate;
3-(para-Methoxyphenyl)-1-propylmercaptyl(2S)-N-(α-toluenesulfonyl)pyrrolidine-2-carboxylate;
3-(para-Methoxyphenyl)-1-propylmercaptyl(2S)-N-(α-toluenesulfonyl)pyrrolidine-2-carboxylate; and
1,5-Diphenyl-3-pentylmercaptyl-N-(para-toluenesulfonyl) pipecolate; or
a pharmaceutically acceptable salt, ester, or solvate thereof.

9. The pharmaceutical composition of claim 1, wherein the compound is of formula II

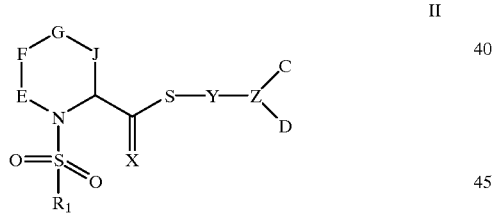

II or a pharmaceutically acceptable salt, ester, or solvate thereof, wherein:
E, F, G and J are independently $CH_2$, O, S, SO, $SO_2$, or $NR$,;
X is either O or S;
Y is a direct bond, $C_1$–$C_6$ straight or branched chain alkyl, or $C_2$–$C_6$ straight or branched chain alkenyl,
wherein any carbon atom of said alkyl or alkenyl is optionally substituted in one or more position(s) with amino, halo, haloalkyl, thiocarbonyl, ester, thioester, alkoxy, alkenoxy, cyano, nitro, imino, alkylamino, aminoalkyl, sulfhydryl, thioalkyl, sulfonyl, or oxygen to form a carbonyl,
or wherein any carbon atom of said alkyl or alkenyl is optionally replaced with O, $NR_2$, S, SO, or $SO_2$;
$R_2$ is selected from the group consisting of hydrogen, $C_1$–$C_4$ straight or branched chain alkyl, $C_3$–$C_4$ straight or branched chain alkenyl or alkynyl, and $C_1$–$C_4$ bridging alkyl, wherein a bridge is formed between the nitrogen and a carbon atom of said alkyl or alkenyl chain having said heteroatom to form a ring,
wherein said ring is optionally fused to an Ar group;
Z is a direct bond, $C_1$–$C_6$ straight or branched chain alkyl, or $C_2$–$C_6$ straight or branched chain alkenyl,
wherein any carbon atom of said alkyl or alkenyl is optionally substituted in one or more position(s) with amino, halo, haloalkyl, thiocarbonyl, ester, thioester, alkoxy, alkenoxy, cyano, nitro, imino, alkylamino, aminoalkyl, sulfhydryl, thioalkyl, sulfonyl, or oxygen to form a carbonyl,
or wherein any atom of said alkyl or alkenyl is optionally replaced with O, $NR_2$, S, SO, or $SO_2$;
Ar is an alicyclic or aromatic, mono-, bi- or tricyclic, carbo- or heterocyclic ring,
wherein the ring is either unsubstituted or substituted with one or more substituent(s),
wherein the individual ring size is 5–8 members,
wherein the heterocyclic ring has 1–6 heteroatom(s) independently selected from the group consisting of O, N, and S;
wherein an aromatic or tertiary alkyl amine is optionally oxidized to a corresponding N-oxide;
C and D are independently hydrogen, Ar, $C_1$–$C_6$ straight or branched chain alkyl, or $C_2$–$C_6$ straight or branched chain alkenyl,
wherein said alkyl or alkenyl is optionally substituted with one or more substituent(s) independently selected from the group consisting of $C_3$–$C_8$ cycloalkyl, $C_5$–$C_7$ cycloalkenyl, oxygen to form a carbonyl, Ar, $C_1$–$C_6$ alkyl, $C_2$–$C_6$ alkenyl, hydroxy, amino, halo, haloalkyl, thiocarbonyl, ester, thioester, alkoxy, alkenoxy, cyano, nitro, imino, alkylamino, aminoalkyl, sulfhydryl, thioalkyl, and sulfonyl,
wherein said cycloalkyl or cycloalkenyl is optionally substituted with $C_1$–$C_4$ alkyl, $C_2$–$C_4$ alkenyl, or hydroxy, amino, halo, haloalkyl, thiocarbonyl, ester, thioester, alkoxy, alkenoxy, cyano, nitro, imino, alkylamion, aminoalkyl, sulfhydryl, thioalkyl, or sulfonyl, or
wherein any carbon atom of said alkyl or alkenyl is optionally replaced with O, $NR_2$, S, SO, or $SO_2$; and
$R_1$, is selected from the group consisting of Ar, $C_3$–$C_8$ cycloalkyl, $C_1$–$C_6$ straight or branched chain alkyl, and $C_2$–$C_6$ straight or branched chain alkenyl,
wherein said alkyl or alkenyl is optionally substituted with one or more substituent(s) independently selected from the group consisting of Ar and $C_3$–$C_8$ cycloalkyl.

10. The pharmaceutical composition of claim 9, wherein the mono- or bicyclic, carbo- or heterocyclic ring is selected from the group consisting of phenyl, benzyl, naphthyl, indolyl, pyridyl, pyrrolyl, pyrrolidinyl, pyridinyl, pyrimidinyl, purinyl, quinolinyl, isoquinolinyl, furyl, fluorenyl, thiophenyl, imidazolyl, oxazolyl, thiazolyl, pyrazolyl, and thienyl.

11. The pharmaceutical composition of claim 1, wherein the compound is of formula III

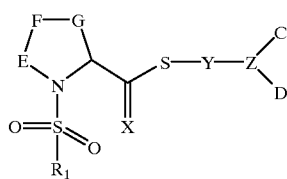

III or a pharmaceutically acceptable salt, ester, or solvate thereof, wherein:

E, F, and G are independently $CH_2$, O, S, SO, $SO_2$, NH or $NR_2$;

X is either O or S;

Y is a direct bond, $C_1$–$C_6$ straight or branched chain alkyl, or $C_2$–$C_6$ straight or branched chain alkenyl,
wherein any carbon atom of said alkyl or alkenyl is optionally substituted in one or more position(s) with amino, halo, haloalkyl, thiocarbonyl, ester, thioester, alkoxy, alkenoxy, cyano, nitro, imino, alkylamino, aminoalkyl, sulfhydryl, thioalkyl, sulfonyl, or oxygen to form a carbonyl,
or wherein any carbon atom of said alkyl or alkenyl is optionally replaced with O, $NR_2$, S, SO, or $SO_2$;

$R_2$ is selected from the group consisting of hydrogen, $C_1$–$C_4$ straight or branched chain alkyl, $C_3$–$C_4$ straight or branched chain alkenyl or alkynyl, and $C_1$–$C_4$ bridging alkyl,
wherein a bridge is formed between the nitrogen and a carbon atom of said alkyl or alkenyl chain having said heteroatom to form a ring,
wherein said ring is optionally fused to an Ar group;

Ar is an alicyclic or aromatic, mono-, bi- or tricyclic, carbo- or heterocyclic ring,
wherein the ring is either unsubstituted or substituted with one or more substituent(s),
wherein the individual ring size is 5–8 members,
wherein the heterocyclic ring has 1–6 heteroatom(s) independently selected from the group consisting of O, N, and S,
wherein an aromatic or tertiary alkyl amine is optionally oxidized to a corresponding N-oxide;

Z is a direct bond, $C_1$–$C_6$ straight or branched chain alkyl, or $C_2$–$C_6$ straight or branched chain alkenyl,
wherein any carbon atom of said alkyl or alkenyl is optionally substituted in one or more position(s) with amino, halo, haloalkyl, thiocarbonyl, ester, thioester, alkoxy, alkenoxy, cyano, nitro, imino, alkylamino, aminoalkyl, sulfhydryl, thioalkyl, sulfonyl, or oxygen to form a carbonyl,
or wherein any atom of said alkyl or alkenyl is optionally replaced with O, $NR_2$, S, SO, or $SO_2$;

C and D are independently hydrogen, Ar, $C_1$–$C_6$ straight or branched chain alkyl, or $C_2$–$C_6$ straight or branched chain alkenyl,
wherein said alkyl or alkenyl is optionally substituted with one or more substituent(s) independently selected from the group consisting of $C_3$–$C_8$ cycloalkyl, $C_5$–$C_7$ cycloalkenyl, oxygen to form a carbonyl, Ar, $C_1$–$C_4$ alkyl, $C_2$–$C_4$ alkenyl, hydroxy, amino, halo, haloalkyl, thiocarbonyl, ester, thioester, alkoxy, alkenoxy, cyano, nitro, imino, alkylamino, aminoalkyl, sulfhydryl, thioalkyl, or sulfonyl,
wherein said cycloalkyl or cycloalkenyl is optionally substituted with $C_1$–$C_4$ alkyl, $C_2$–$C_4$ alkenyl, hydroxy, amino, halo, haloalkyl, thiocarbonyl, ester thioester, alkoxy, alkenoxy, cyano, nitro, imino, alkylamino, aminoalkyl, sulfhydryl, thioalkyl, or sulfonyl, or
wherein any carbon atom of said alkyl or alkenyl is optionally replaced with O, $NR_2$, S, SO, or $SO_2$; and $R_1$ is selected from the group consisting of Ar, $C_3$–$C_8$ cycloalkyl, $C_1$–$C_6$ straight or branched chain alkyl, and $C_2$–$C_6$ straight or branched chain alkenyl,
wherein said alkyl or alkenyl is optionally substituted with one or more substituent(s) independently selected from the group consisting of Ar and $C_3$–$C_8$ cycloalkyl.

12. The pharmaceutical composition of claim 11, wherein the mono- or bicyclic, carbo- or heterocyclic ring is selected from the group consisting of phenyl, benzyl, naphthyl, indolyl, pyridyl, pyrrolyl, pyrrolidinyl, pyridinyl, pyrimidinyl, purinyl, quinolinyl, isoquinolinyl, furyl, fluorenyl, thiophenyl, imidazolyl, oxazolyl, thiazolyl, pyrazolyl, and thienyl.

13. The pharmaceutical composition of claim 1, wherein the compound is of formula IV

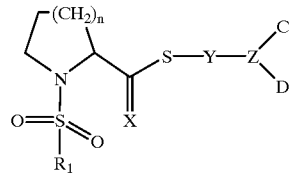

IV or a pharmaceutically acceptable salt, ester, or solvate thereof, wherein:

n is 1, 2 or 3;

X is either O or S;

Y is a direct bond, $C_1$–$C_6$ straight or branched chain alkyl, or $C_2$–$C_6$ straight or branched chain alkenyl,
wherein any carbon atom of said alkyl or alkenyl is optionally substituted in one or more position(s) with amino, halo, haloalkyl, thiocarbonyl, ester, thioester, alkoxy, alkenoxy, cyano, nitro, imino, alkylamino, aminoalkyl, sulfhydryl, thioalkyl, sulfonyl, or oxygen to form a carbonyl,
or wherein any carbon atom of said alkyl or alkenyl is optionally replaced with O, $NR_2$, S, SO, or $SO_2$;

$R_2$ is selected from the group consisting of hydrogen, $C_1$–$C_4$ straight or branched chain alkyl, $C_3$–$C_4$ straight or branched chain alkenyl or alkynyl, and $C_1$–$C_4$ bridging alkyl,
wherein a bridge is formed between the nitrogen and a carbon atom of said alkyl or alkenyl chain having said heteroatom to form a ring,
wherein said ring is optionally fused to an Ar group;

Z is a direct bond, $C_1$–$C_6$ straight or branched chain alkyl, or $C_2$–$C_6$ straight or branched chain alkenyl,
wherein any carbon atom of said alkyl or alkenyl is optionally substituted in one or more position(s) with amino, halo, haloalkyl, thiocarbonyl, ester, thioester, alkoxy, alkenoxy, cyano, nitro, imino, alkylamino, aminoalkyl, sulfhydryl, thioalkyl, sulfonyl, or oxygen to form a carbonyl,
or wherein any atom of said alkyl or alkenyl is optionally replaced with O, $NR_2$, S, SO, or $SO_2$;

Ar is an alicyclic or aromatic, mono-, bi- or tricyclic, carbo- or heterocyclic ring,
wherein the ring is either unsubstituted or substituted with one or more substituent(s), wherein the individual ring size is 5–8 members,
wherein the heterocyclic ring has 1–6 heteroatom(s) independently selected from the group consisting of O, N, and S,
wherein an aromatic or tertiary alkyl amine is optionally oxidized to a corresponding N-oxide;
C and D are independently hydrogen, Ar, $C_1$–$C_6$ straight or branched chain alkyl, or $C_2$–$C_6$ straight or branched chain alkenyl,
wherein said alkyl or alkenyl is optionally substituted with one or more substituent(s) independently selected from the group consisting of $C_3$–$C_8$ cycloalkyl, $C_5$–$C_7$ cycloalkenyl, oxygen to form a carbonyl, Ar, $C_1$–$C_4$ alkyl, $C_2$–$C_4$ alkenyl, hydroxy, amino, halo, haloalkyl, thiocarbonyl, ester, thioester, alkoxy, alkenoxy, cyano, nitro, imino, alkylamino, aminoalkyl, sulfhydryl, thioalkyl, or sulfonyl,
wherein said cycloalkyl or cycloalkenyl is optionally substituted with $C_1$–$C_4$ alkyl, $C_2$–$C_4$ alkenyl, hydroxy, amino, halo, haloalkyl, thiocarbonyl, ester, thioester, alkoxy, alkenoxy, cyano, nitro, imino, alkylamino, aminoalkyl, sulfhydryl, thioalkyl, or sulfonyl, or
wherein any carbon atom of said alkyl or alkenyl is optionally replaced with O, $NR_2$, S, SO, or $SO_2$; and
$R_1$ is selected from the group consisting of Ar, $C_3$–$C_8$ cycloalkyl, $C_1$–$C_6$ straight or branched chain alkyl, and $C_2$–$C_6$ straight or branched chain alkenyl,
wherein said alkyl or alkenyl is optionally substituted with one or more substituent(s) independently selected from the group consisting of Ar and $C_3$–$C_8$ cycloalkyl.

14. The pharmaceutical composition of claim 13, wherein the mono- or bicyclic, carbo- or heterocyclic ring is selected from the group consisting of phenyl, benzyl, naphthyl, indolyl, pyridyl, pyrrolyl, pyrrolidinyl, pyridinyl, pyrimidinyl, purinyl, quinolinyl, isoquinolinyl, furyl, fluorenyl, thiophenyl, imidazolyl, oxazolyl, thiazolyl, pyrazolyl, and thienyl.

15. A pharmaceutical composition which comprises:
(i) a compound of formula V

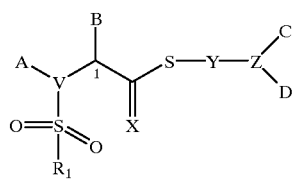

or a pharmaceutically acceptable salt, ester, or solvate thereof, wherein:
V is C, N, or S;
A and B, taken together with the nitrogen and carbon atoms to which they are respectively attached, form a 5–7 membered saturated or unsaturated heterocyclic ring comprising one or more O, S, SO, $SO_2$, N, or $NR_2$ heteroatom(s);
X is either O or S;
Y is a direct bond, $C_1$–$C_6$ straight or branched chain alkyl, or $C_2$–$C_6$ straight or branched chain alkenyl,
wherein any carbon atom of said alkyl or alkenyl is optionally substituted in one or more positions) with amino, halo, haloalkyl, thiocarbonyl, ester, thioester, alkoxy, alkenoxy, cyano, nitro, imino, alkylamino, aminoalkyl, sulfhydryl, thioalkyl, sulfonyl, or oxygen to form a carbonyl,
or wherein any carbon atom of said alkyl or alkenyl is optionally replaced with O, $NR_2$, S, SO, or $SO_2$;

R, is selected from the group consisting of hydrogen, $C_1$–$C_4$ straight or branched chain alkyl, $C_3$–$C_4$ straight or branched chain alkenyl or alkynyl, and $C_1$–$C_4$ bridging alkyl,
wherein a bridge is formed between the nitrogen and a carbon atom of said alkyl or alkenyl chain comprising said heteroatom to form a ring,
wherein said ring is optionally fused to an Ar group;
Ar is an alicyclic or aromatic, mono-, bi- or tricyclic, carbo- or heterocyclic ring,
wherein the ring is either unsubstituted or substituted with one or more substituent(s),
wherein the individual ring size is 5–8 members,
wherein the heterocyclic ring contains 1–6 heteroatom(s) independently selected from the group consisting of O, N, and S,
wherein an aromatic or tertiary alkyl amine is optionally oxidized to a corresponding N-oxide;
Z is a direct bond, $C_1$–$C_6$ straight or branched chain alkyl, or $C_2$–$C_6$ straight or branched chain alkenyl,
wherein any carbon atom of said alkyl or alkenyl is optionally substituted in one or more position(s) with amino, halo, haloalkyl, thiocarbonyl, ester, thioester, alkoxy, alkenoxy, cyano, nitro, imino, alkylamino, aminoalkyl, sulfhydryl, thioalkyl, sulfonyl, or oxygen to form a carbonyl,
or wherein any atom of said alkyl or alkenyl is optionally replaced with O, $NR_2$, S, SO, or $SO_2$;
C and D are independently hydrogen, Ar, $C_1$–$C_6$ straight or branched chain alkyl, or $C_2$–$C_6$ straight or branched chain alkenyl,
wherein said alkyl or alkenyl is optionally substituted with one or more substituent(s) independently selected from the group consisting of $C_3$–$C_8$ cycloalkyl, $C_5$–$C_7$ cycloalkenyl, oxygen to form a carbonyl, Ar, $C_1$–$C_6$ alkyl, $C_2$–$C_6$ alkenyl, hydroxy, amino, halo, haloalkyl, thiocarbonyl, ester, thioester, alkoxy, alkenoxy, cyano, nitro, imino, alkylamino, aminoalkyl, sulfhydryl, thioalkyl, and sulfonyl,
wherein said cycloalkyl or cycloalkenyl is optionally substituted with $C_1$–$C_6$ alkyl, $C_2$–$C_6$ alkenyl, hydroxy, amino, halo, haloalkyl, thiocarbonyl, ester, thioester, alkoxy, alkenoxy, cyano, nitro, imino, alkylamino, aminoalkyl, sulfhydryl, thioalkyl, or sulfonyl, or
wherein any carbon atom of said alkyl or alkenyl is optionally replaced with O, $NR_2$, S, SO, or $SO_2$;
$R_1$ is selected from the group consisting of Ar, $C_3$–$C_8$ cycloalkyl, $C_1$–$C_6$ straight or branched chain alkyl, and $C_2$–$C_6$ straight or branched chain alkenyl,
wherein said alkyl or alkenyl is optionally substituted with one or more substituent(s) independently selected from the group consisting of Ar, $C_3$–$C_8$ cycloalkyl, amino, halo, haloalkyl, hydroxy, trifluoromethyl, $C_1$–$C_6$ straight or branched chain alkyl, $C_2$–$C_6$ straight or branched chain alkenyl, carbonyl, thiocarbonyl, ester, thioester, alkoxy, alkenoxy, cyano, nitro, imino, alkylamino, aminoalkyl, sulfhydryl, thioalkyl, and sulfonyl,
wherein any carbon atom of said alkyl or alkenyl is optionally replaced with O, $NR_2$, S, SO, or $SO_2$, for treating alopecia or promoting hair growth in an animal;
(ii) a second alopecia treating or hair growth promoting compound; and
(iii) a pharmaceutically acceptable carrier.

* * * * *